(12) United States Patent
Sanai et al.

(10) Patent No.: US 9,993,665 B2
(45) Date of Patent: Jun. 12, 2018

(54) TREATMENT INSTRUMENT, DISTAL SIDE PROBE UNIT, AND PROXIMAL SIDE PROBE UNIT

(71) Applicant: OLYMPUS CORPORATION, Hachioji-shi, Tokyo (JP)

(72) Inventors: Hideo Sanai, Hachioji (JP); Kenichi Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days. days.

(21) Appl. No.: 15/287,466

(22) Filed: Oct. 6, 2016

(65) Prior Publication Data

US 2017/0021199 A1 Jan. 26, 2017

Related U.S. Application Data

(63) Continuation of application No. PCT/JP2015/062592, filed on Apr. 24, 2015.

(30) Foreign Application Priority Data

Sep. 5, 2014 (JP) ................................. 2014-181394

(51) Int. Cl.
*A61N 7/00* (2006.01)
*A61B 17/32* (2006.01)
(Continued)

(52) U.S. Cl.
CPC ........ *A61N 7/00* (2013.01); *A61B 17/320068* (2013.01); *A61B 2017/00473* (2013.01);
(Continued)

(58) Field of Classification Search
CPC ................................................. A61B 2017/293
See application file for complete search history.

(56) References Cited

U.S. PATENT DOCUMENTS 6,068,647 A 5/2000 Witt et al.
6,328,703 B1 12/2001 Murakami
(Continued)

FOREIGN PATENT DOCUMENTS

EP 2 074 959 A1 7/2009
EP 2 100 563 A1 9/2009
(Continued)

OTHER PUBLICATIONS

Jul. 21, 2015 Search Report issued in International Patent Application No. PCT/JP2015/062592.
(Continued)

*Primary Examiner* — Luther G Behringer
(74) *Attorney, Agent, or Firm* — Oliff PLC

(57) ABSTRACT

A treatment instrument includes: a proximal side probe transmits ultrasonic vibration from its proximal end to its distal end; a distal side probe configured to transmit the ultrasonic vibration from its proximal end to a treatment portion at its distal end; and a holding portion which holds a state where the proximal end of the distal side probe is into collision with the distal end of the proximal side probe, and a state where vibration is transmittable from the proximal end of the proximal side probe to the distal end of the distal side probe.

21 Claims, 23 Drawing Sheets

(51) Int. Cl.
 *A61B 17/00* (2006.01)
 *A61B 17/29* (2006.01)
(52) U.S. Cl.
 CPC .............. *A61B 2017/00477* (2013.01); *A61B 2017/293* (2013.01); *A61B 2017/2929* (2013.01)

(56) References Cited

U.S. PATENT DOCUMENTS

| | | | |
|---|---|---|---|
| 2004/0097911 A1* | 5/2004 | Murakami | A61B 17/320092 |
| | | | 606/27 |
| 2010/0298743 A1 | 11/2010 | Nield et al. | |
| 2011/0118631 A1 | 5/2011 | Onaga | |
| 2013/0324991 A1 | 12/2013 | Clem et al. | |

FOREIGN PATENT DOCUMENTS

| | | |
|---|---|---|
| EP | 2 635 203 A1 | 9/2013 |
| JP | 2001-008943 A | 1/2001 |
| JP | 2001-017442 A | 1/2001 |
| JP | 2001-314412 A | 11/2001 |
| JP | 2012-527325 A | 11/2012 |
| WO | 2011/016305 A1 | 2/2011 |

OTHER PUBLICATIONS

March 16, 2017 Noticification of Transmittal of Translation of IPRP issued in International Patent Application No. PCT/JP2015/062592.
Mar. 7, 2018 Extended European Search Report issued in European Patent Application No. 15838190.5.

\* cited by examiner

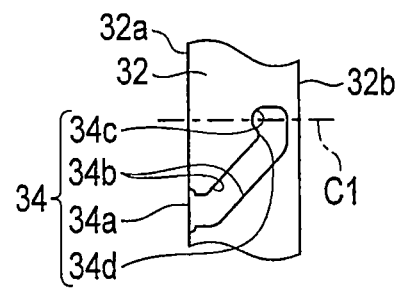
F I G. 1B
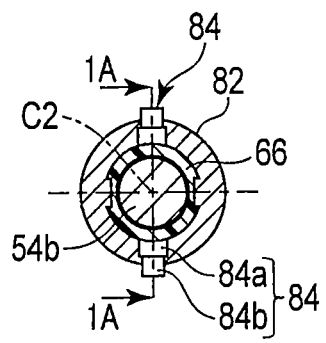
F I G. 1C
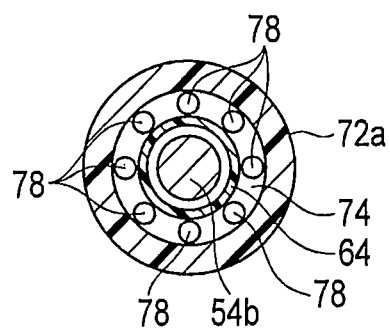
F I G. 1D

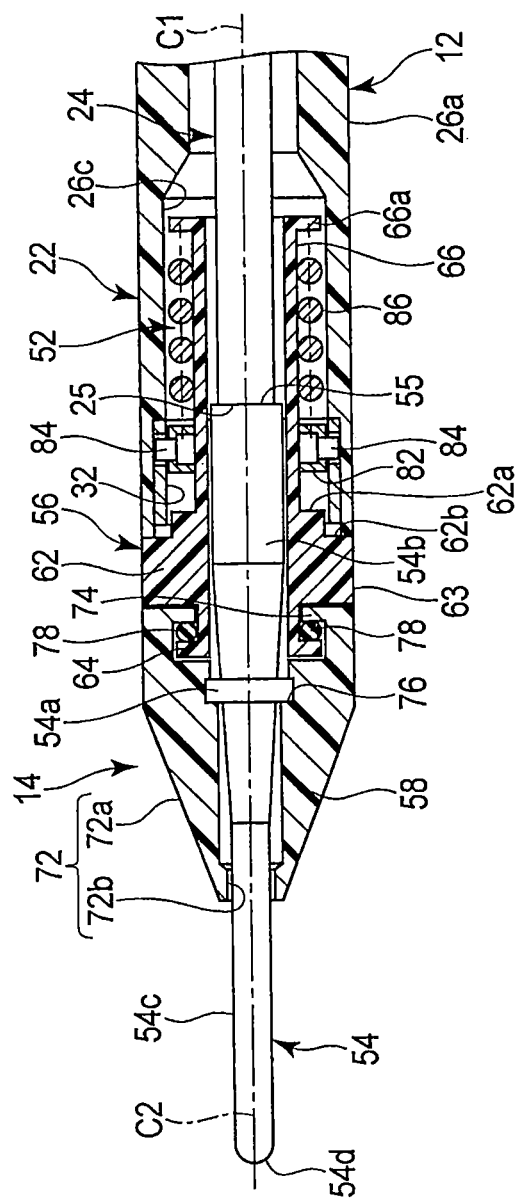
F I G. 2A

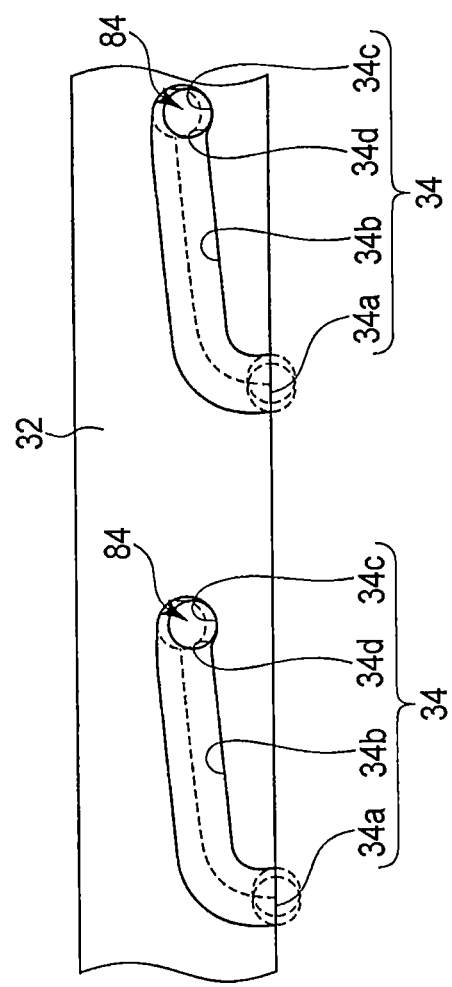
F I G. 2B

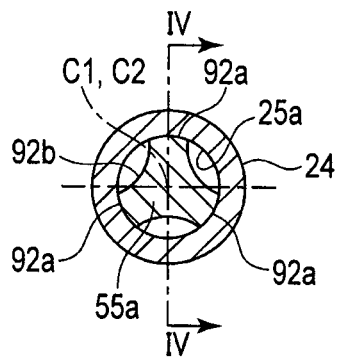
F I G. 5A
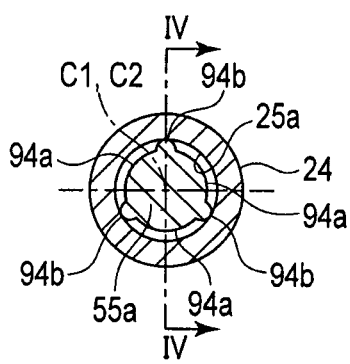
F I G. 5B
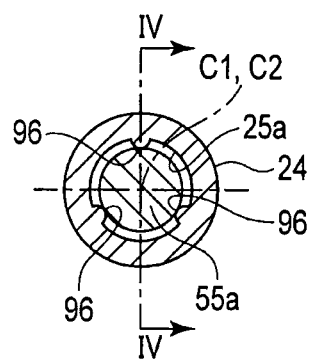
F I G. 5C

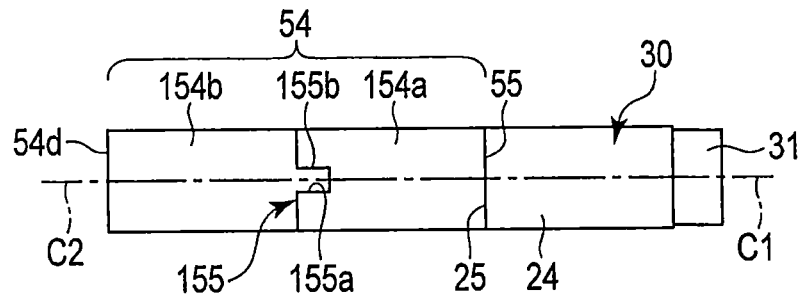
F I G. 6A
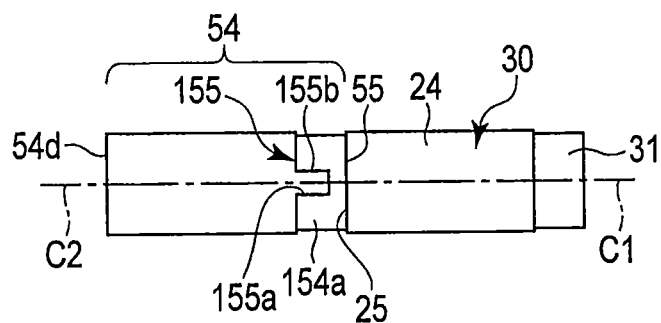
F I G. 6B
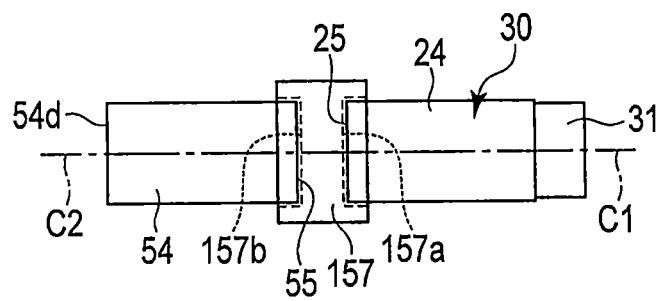
F I G. 6C

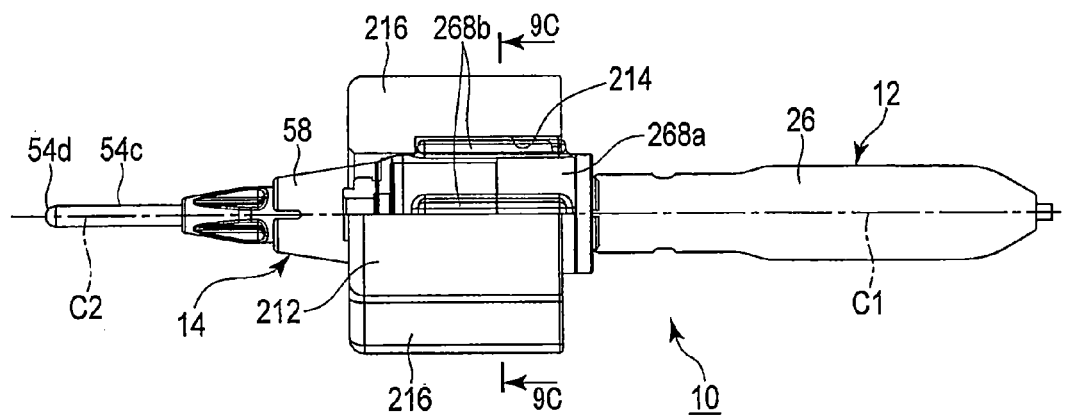
F I G. 9B
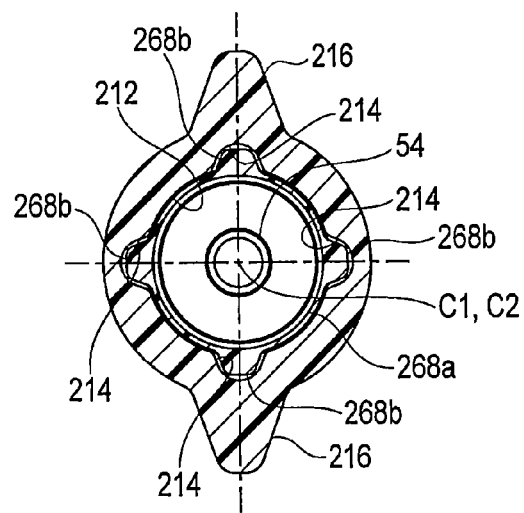
F I G. 9C

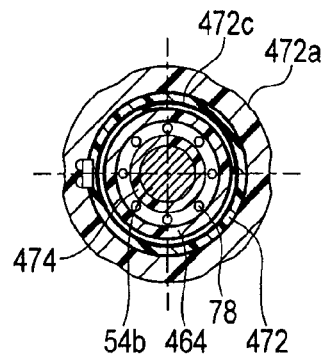
F I G. 13E
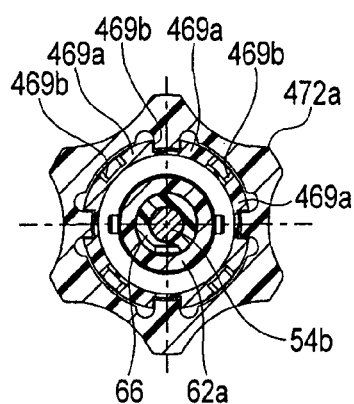
F I G. 13F
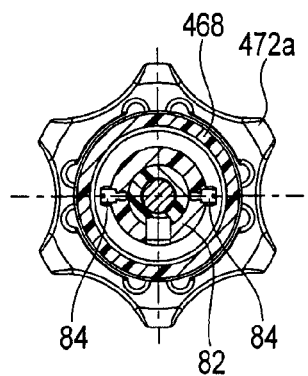
F I G. 13G

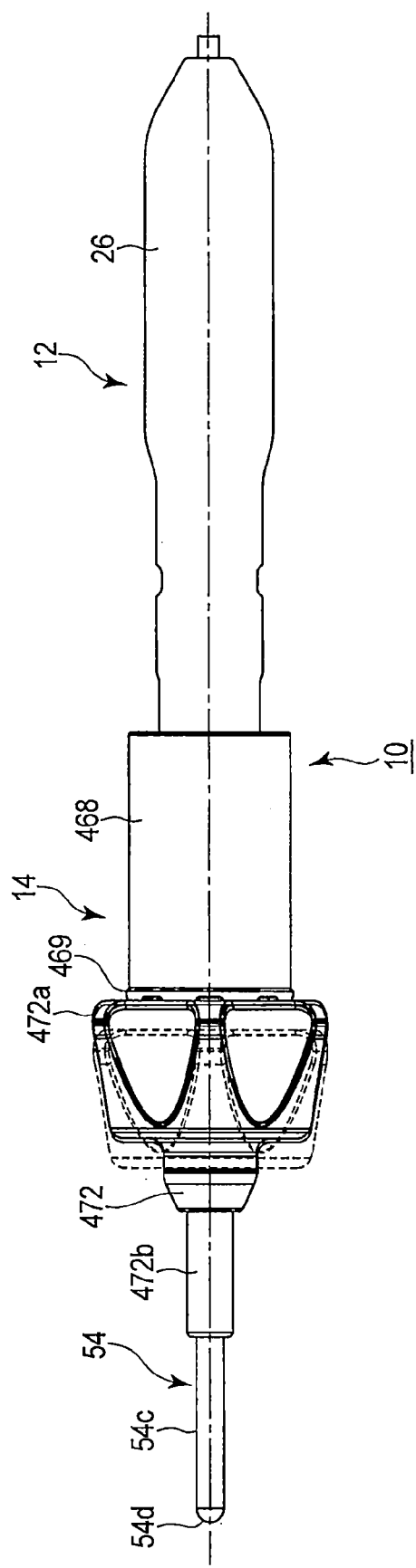
F I G. 14B

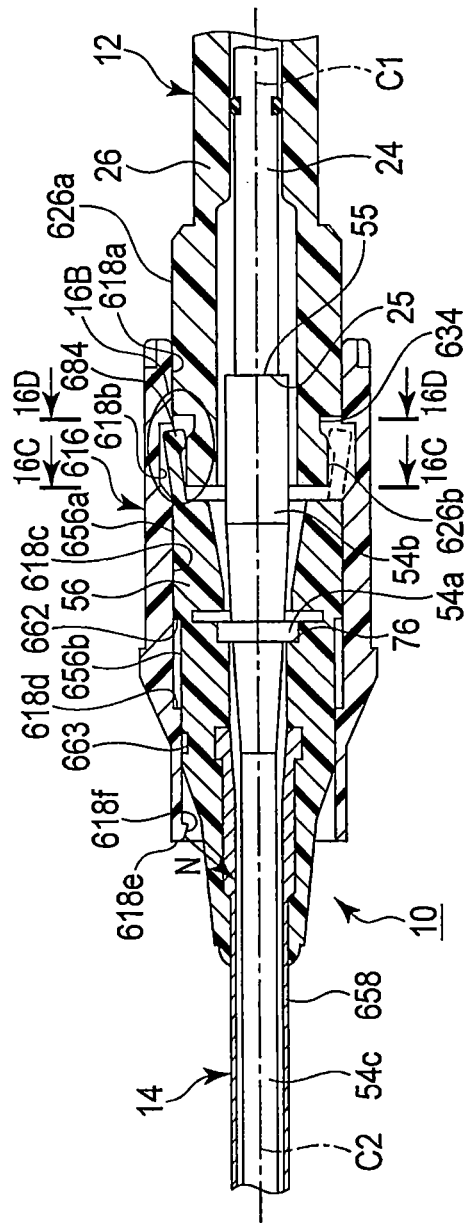
F I G. 16A

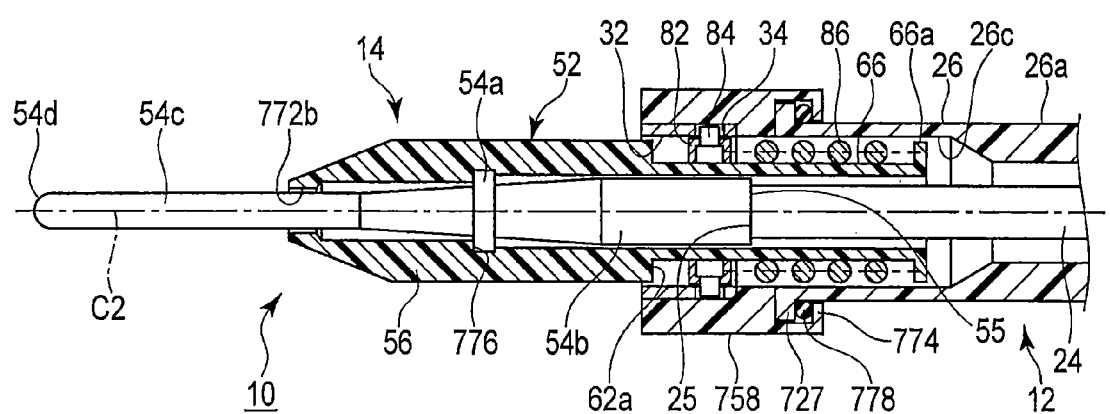
F I G. 18

TREATMENT INSTRUMENT, DISTAL SIDE PROBE UNIT, AND PROXIMAL SIDE PROBE UNIT

CROSS-REFERENCE TO RELATED APPLICATIONS

This application is a Continuation application of PCT Application No. PCT/JP2015/062592, filed Apr. 24, 2015 and based upon and claiming the benefit of priority from prior Japanese Patent Application No. 2014-181394, filed Sep. 5, 2014, the entire contents of all of which are incorporated herein by reference.

BACKGROUND OF THE INVENTION

1. Field of the Invention

This invention relates to a treatment instrument, a distal side probe unit, and a proximal side probe unit.

2. Description of the Related Art

For example, in an ultrasonic treatment instrument disclosed in the specification of U.S. Pat. No. 6,068,647, the distal side of a proximal side ultrasonic probe which transmits ultrasonic vibration from an ultrasonic transducer from the proximal end to the distal end, and the proximal end of a distal side ultrasonic probe having a treatment portion at the distal end are fastened by screws and thus used. A tool such as a torque wrench which connects the distal end of the proximal side ultrasonic probe to the proximal end of the distal side ultrasonic probe with a suitably set torque is used. The ultrasonic treatment instrument disclosed in the specification of U.S. Pat. No. 6,068,647 can rotate the ultrasonic probes together with the ultrasonic transducer to change the direction of the treatment portion if a knob is rotated.

BRIEF SUMMARY OF THE INVENTION

According to one aspect of the present invention, a treatment instrument includes: a proximal side probe which extends along a first central axis defined by its proximal end and its distal end and which transmits ultrasonic vibration from an ultrasonic transducer from the proximal end to the distal end along the first central axis; a distal side probe which extends along a second central axis defined by its proximal end and its distal end, which includes a treatment portion, and which is configured to transmit ultrasonic vibration from the proximal end to the treatment portion at the distal end of the distal side probe along the second central axis; a holding portion which holds a state where the proximal end of the distal side probe is into collision with the distal end of the proximal side probe, and a state where vibration from the ultrasonic transducer is transmittable from the proximal end of the proximal side probe to the distal end of the distal side probe, and which holds a state the first central axis is aligned with the second central axis; and an operation portion which is provided in the holding portion and which turns or rotates the distal side probe relative to the proximal side probe around the first central axis and the second central axis by an operation to rotate the distal side probe around the first central axis and the second central axis, to direct the treatment portion at the distal end of the distal side probe in a desired direction.

According to one aspect of the present invention, a distal side probe unit includes: a distal side holding portion which is attachable to and detachable from a proximal side cover in which a proximal side probe is disposed, the proximal side probe defining a first central axis, and transmitting ultrasonic vibration from an ultrasonic transducer from its proximal end to its distal end along the first central axis; and a distal side probe which is held by the distal side holding portion, which defines a second central axis and which is configured to transmit ultrasonic vibration from its proximal end to a treatment portion at the distal end along the second central axis, wherein when the distal side holding portion and the proximal side cover are attached to each other, the distal end of the proximal side probe is brought into collision with the proximal end of the distal side probe in a state where the first central axis is aligned with the second central axis; the distal side probe is configured to transmit the vibration from the ultrasonic transducer from its proximal end to the treatment portion at the distal end in a state where the distal end of the proximal side probe is in collision with the distal side probe; and the distal side probe is configured to turn or rotate relative to the proximal side probe around the first central axis and the second central axis and directs the treatment portion at the distal end of the distal side probe in a desired direction.

According to one aspect of the present invention, a proximal side probe unit includes: a proximal side cover which is attachable to and detachable from a distal side holding portion holding a distal side probe defining a second central axis and being configured to transmit ultrasonic vibration from its proximal end to a treatment portion at the distal end along the second central axis; and a proximal side probe which is disposed inside the proximal side cover, which defines a first central axis and which transmits ultrasonic vibration from an ultrasonic transducer from its proximal end to its distal end along the first central axis, wherein when the proximal side cover is attached to the distal side holding portion, the first and second central axes are aligned, and the distal end of the proximal side probe is brought into collision with the proximal end of the distal side probe; the proximal side probe is configured to transmit the vibration from the ultrasonic transducer from its proximal end to the treatment portion at the distal end of the distal side probe in a state where the proximal end of the distal side probe is in collision with the distal end of the proximal side probe; and the proximal side probe is configured to turn or rotate relative to the distal side probe around the first and second central axes and directs the treatment portion at the distal end of the distal side probe in a desired direction.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1B is a schematic diagram showing a cam ring having a cam groove seen from the direction of an arrow 1B line in FIG. 1A;

FIG. 1C is a schematic cross sectional view taken along the line 1C-1C in FIG. 1A;

FIG. 1D is a schematic cross sectional view taken along the line 1D-1D in FIG. 1A;

FIG. 2A is a schematic longitudinal sectional view showing a state where the proximal side probe unit and the distal side probe unit according to the first embodiment are attached;

FIG. 2B is a development showing a state where a cam pin is disposed in the cam groove;

FIG. 5A is a schematic cross sectional view taken along the line V-V in FIG. 4 showing a state where the distal side collision portion of the proximal side vibration transmission body of the treatment instrument according to the second modification of the first embodiment is in collision with the proximal side collision portion of the distal side vibration transmission body;

FIG. 5B is a schematic cross sectional view taken along the line V-V in FIG. 4 showing a state where the distal side collision portion of the proximal side vibration transmission body of the treatment instrument according to the second modification of the first embodiment is in collision with the proximal side collision portion of the distal side vibration transmission body;

FIG. 5C is a schematic cross sectional view taken along the line V-V in FIG. 4 showing a state where the distal side collision portion of the proximal side vibration transmission body of the treatment instrument according to the second modification of the first embodiment is in collision with the proximal side collision portion of the distal side vibration transmission body;

FIG. 6A is a schematic diagram showing a connection structure of a vibration transmission body which transmits ultrasonic vibration of a treatment instrument according to a third modification of the first embodiment;

FIG. 6B is a schematic diagram showing the connection structure of the vibration transmission body which transmits the ultrasonic vibration of the treatment instrument according to the third modification of the first embodiment;

FIG. 6C is a schematic diagram showing the connection structure of the vibration transmission body which transmits the ultrasonic vibration of the treatment instrument according to the third modification of the first embodiment;

FIG. 9B is a schematic side view showing a state where a jig which can be used in attachment/detachment for the proximal side probe unit is fitted into the distal side probe unit of the treatment instrument in a state where the distal side probe unit is attached to the proximal side probe unit, according to the fifth modification of the first embodiment;

FIG. 9C is a schematic cross sectional view taken along the line 9C-9C in FIG. 9B of the treatment instrument according to the fifth modification of the first embodiment;

FIG. 13E is a schematic cross sectional view taken along the line 13E-13E in FIG. 13A;

FIG. 13F is a schematic cross sectional view taken along the line 13F-13F in FIG. 13A;

FIG. 13G is a schematic cross sectional view taken along the line 13G-13G in FIG. 13A;

FIG. 14B is a schematic side view showing a state where the proximal side probe unit and the distal side probe unit according to the eighth modification of the first embodiment are attached;

FIG. 16A is a schematic longitudinal sectional view showing a state where an adaptor which couples the proximal side probe unit to the distal side probe unit is disposed closer to the distal side than a coupling position while the proximal side probe unit and the distal side probe unit of a treatment instrument according to a third embodiment are disposed on the same central axis;

FIG. 18 is a schematic longitudinal sectional view showing a state where the proximal side probe unit and the distal side probe unit according to the fourth embodiment are attached.

DETAILED DESCRIPTION OF THE INVENTION

Hereinafter, embodiments of this invention will be described with reference to the drawings.

Figure 1A:
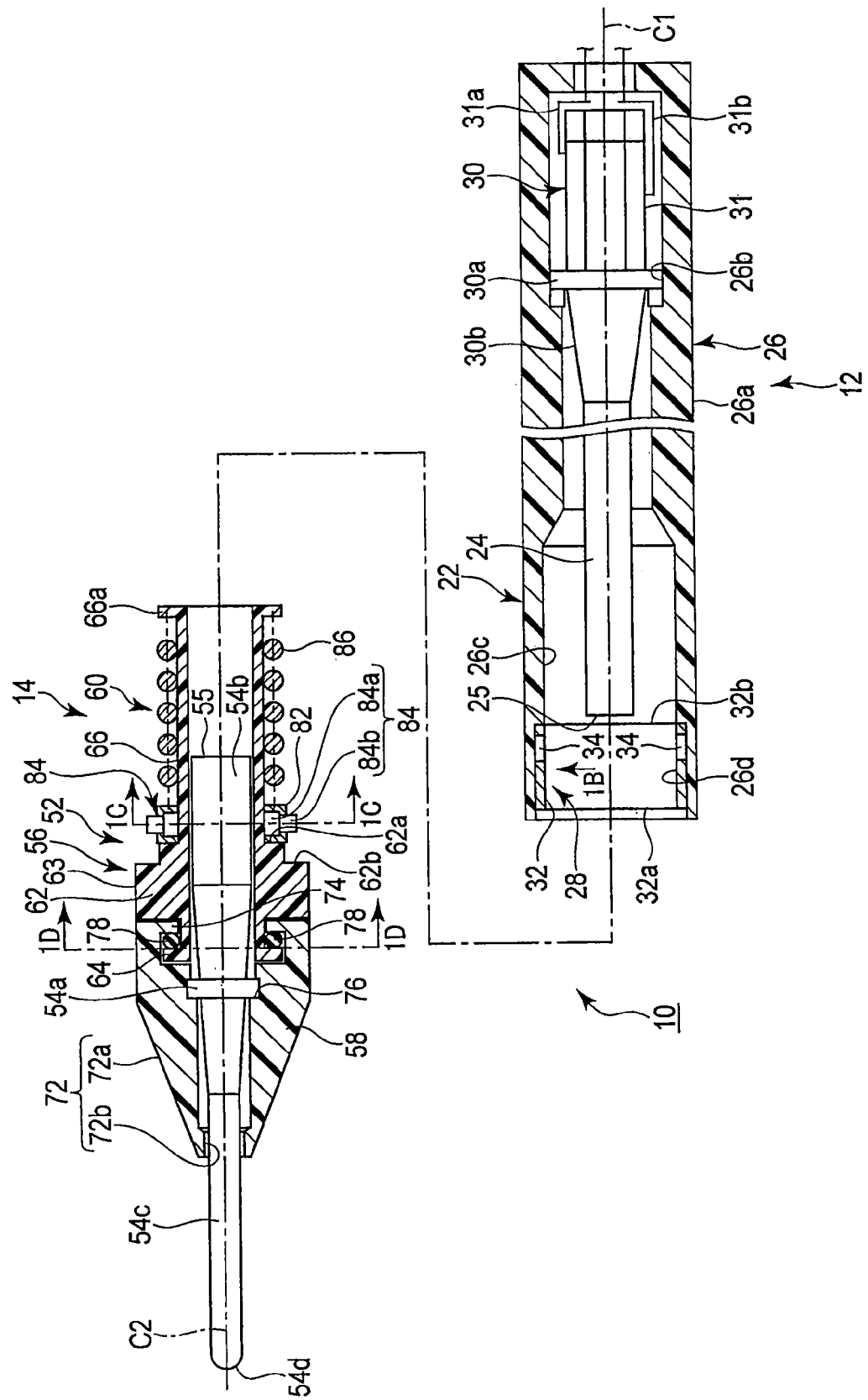
FIG. 1A is a schematic longitudinal sectional view showing a state where a proximal side probe unit and a distal side probe unit according to a first embodiment are separated.

As shown in FIG. 1A, a treatment instrument 10 according to this embodiment includes a proximal side probe unit (ultrasonic transducer unit) 12, and a distal side probe unit 14. The proximal side probe unit 12 and the distal side probe unit 14 are attachable to and detachable from each other.

The proximal side probe unit 12 according to this embodiment includes a proximal side holding portion (proximal side cover) 22, and a proximal side vibration transmission body (proximal side probe) 24. The proximal side holding portion 22 has an exterior case 26 and a first connection portion 28.

The proximal side vibration transmission body 24 is made of a metallic material having satisfactory acoustic characteristics such as a titanium alloy material, a stainless alloy material, or an aluminum alloy material. The proximal side vibration transmission body 24 defines a central axis C1 by its proximal end and its distal end. In this embodiment, the central axis C1 is preferably straight. In this embodiment, an ultrasonic transducer unit 30 is disposed continuously with the proximal end of the proximal side vibration transmission body 24.

The ultrasonic transducer unit 30 has a flange portion (transducer seat) 30a supported in a whirl-stopped state on a later-described support portion 26b of the inner circumferential surface of the exterior case 26, an ultrasonic transducer 31 fixed to the proximal side of the flange portion 30a, and a horn 30b which is integrally formed at the distal end of the flange portion 30a and which amplifies ultrasonic vibration generated in the ultrasonic transducer 31. In this embodiment, the proximal side vibration transmission body 24 is integrally formed at the distal end of the horn 30b.

The flange portion (support portion) 30a is formed into a shape other than a circular shape. For example, the ultrasonic transducer 31 of a known BLT type is disposed at the proximal end of the flange portion 30a. The ultrasonic transducer 31 is firmly fixed to the proximal end of the flange portion 30a. The ultrasonic transducer 31 vibrates when a suitable electric current is supplied to the ultrasonic transducer 31 from an electric power supply (not shown) through electric power supply cords 31a and 31b extending from the ultrasonic transducer 31.

In the ultrasonic transducer unit 30, the horn 30b is integrally formed on the distal side of the flange portion 30a. The horn 30b tapers off from the proximal side to the distal side along the central axis C1, and increases the amplitude of ultrasonic vibration generated in the ultrasonic transducer 31. The proximal side vibration transmission body 24 on the distal side of the horn 30b maintains a substantially constant outside diameter.

The proximal side vibration transmission body 24 has, at its distal end, a distal side collision portion (distal surface) 25 which is brought into collision with a later-described proximal side collision portion (proximal surface) 55 of the distal side probe unit 14. In this embodiment, the distal side collision portion 25 is formed as a surface that intersects at right angles with the central axis C1.

The exterior case 26 is preferably made of a plastic material having heat-resistant and electrically-insulating properties. The exterior case 26 has a cylindrically formed main body 26a. The support portion 26b which supports the flange portion 30a of the ultrasonic transducer unit 30 in a whirl-stopped state is formed in the main body 26a. In a state where the proximal side vibration transmission body 24 is disposed in the main body 26a of the exterior case 26, the central axis C1 of the proximal side vibration transmission body 24 is aligned with the central axis of the exterior case 26.

In this embodiment, the distal-side inner circumferential surface along the central axis C1 in the main body 26a of the exterior case 26 is formed as a housing portion 26c to receive a later-described base body 56 of the distal side probe unit 14.

An annular recess 26d is formed in the inner circumferential surface of the distal end of the main body 26a of the exterior case 26, that is, in the inner circumferential surface of the distal end of the housing portion 26c. The first connection portion (proximal side connection portion) 28 is fixed to the annular recess 26d.

The first connection portion 28 includes a cam ring 32 fixed to the annular recess 26d at the distal end of the main body 26a of the exterior case 26, and a cam groove 34 formed in the cam ring 32. The cam ring 32 is suitably fixed, for example, by screwing to the distal end of the main body 26a of the exterior case 26. The cam ring 32 includes a distal edge 32a at the distal end and a proximal edge 32b at the proximal end along the central axis C1. The proximal edge 32b of the cam ring 32 abuts on the annular recess 26d of the exterior case 26 so that the movement to the proximal side along the central axis C1 is regulated.

As shown in FIG. 1B, the cam groove 34 has an opening 34a formed in the distal edge 32a of the cam ring 32. The opening width of the opening 34a along the circumferential direction of the cam ring 32 is formed to be slightly greater than the outside diameter of a later-described cam pin 84. A facing inclined plane 34b is continuously formed in the opening 34a. The width of the inclined plane 34b is formed to be slightly greater than the outside diameter of the cam pin 84. An engagement portion 34c which holds the cam pin 84 in an engagement state is formed continuously with the inclined plane 34b at the proximal end of the opening 34a of the cam groove 34. A movement regulation portion 34d which regulates the movement of the cam pin 84 from the engagement portion 34c to the inclined plane 34b is formed between the inclined plane 34b and the engagement portion 34c.

One cam groove 34 may be provided, but more than one cam groove 34, for example, two or three cam grooves 34 are also preferable. In this embodiment, as shown in FIG. 1A, a pair of cam grooves 34 face each other with respect to the central axis C1. It is also preferable for the cam grooves 34 to be formed at suitable positions, for example, at positions located 90 degrees apart relative to the central axis C1.

The distal side probe unit 14 according to this embodiment includes a distal side holding portion 52 which is attachable to and detachable from the proximal side holding portion 22, and a distal side vibration transmission body (distal side probe) 54. The distal side holding portion 52 includes the base body 56, a rotation knob (sheath) 58, and a second connection portion (distal side connection portion) 60.

The distal side vibration transmission body 54 is made of a metallic material having satisfactory acoustic characteristics such as a titanium alloy material, a stainless alloy material, or an aluminum alloy material. For example, a titanium alloy material having the same components is used for the proximal side vibration transmission body 24 of the proximal side probe unit 12 and the distal side vibration transmission body 54 of the distal side probe unit 14 described in this embodiment. Naturally, the same titanium alloy material is also used for the flange portion 30a and the horn 30b of the ultrasonic transducer unit 30 that are formed integrally with the proximal side vibration transmission body 24 in this embodiment.

The distal side vibration transmission body 54 defines a central axis C2 by its proximal end and its distal end.

In this embodiment, the central axis C2 is preferably straight. The distal side vibration transmission body 54 has a flange portion 54a formed between its proximal end and its distal end. The flange portion 54a is formed into a shape other than a circular shape.

In the distal side vibration transmission body 54, a first vibration transmitting portion 54b capable of transmitting vibration from the proximal side to the distal side is formed on the proximal side of the flange portion 54a. The first vibration transmitting portion 54b of the distal side vibration transmission body 54 has, at its proximal end, the proximal side collision portion 55 which is directly brought into collision with the distal side collision portion 25 of the proximal side probe unit 12. The proximal side collision portion 55 is formed as a surface that intersects at right angles with the central axis C2.

The outside diameter of the proximal side collision portion 55 of the distal side vibration transmission body 54 is preferably formed to be the same as or slightly larger than the outside diameter of the distal side collision portion 25 of the proximal side vibration transmission body 24. The outside diameter of the proximal side collision portion 55 of the distal side vibration transmission body 54 may be formed to be slightly smaller than the outside diameter of the distal side collision portion 25 of the proximal side vibration transmission body 24.

In the distal side vibration transmission body 54, a second vibration transmitting portion 54c capable of transmitting vibration from the proximal side to the distal side is formed on the distal side of the flange portion 54a. A treatment portion 54d to treat a living tissue is formed at the distal end of the second vibration transmitting portion 54c. The treatment portion 54d can be, for example, of a blade shape, a hook shape, or a spatula shape in accordance with a treatment target. The treatment portion 54d may be suitably bent at the distal end of the second vibration transmitting portion 54c.

Each of the first vibration transmitting portion 54b and the second vibration transmitting portion 54c may maintain a substantially constant outside diameter from its proximal end to distal end, and may be formed in at least one part so that the outside diameter is reduced from the proximal end to the distal end as shown in FIG. 1A.

The base body 56 is formed into a cylindrical shape through which the distal side vibration transmission body 54 is inserted. The base body 56 is preferably made of a plastic material having heat-resistant and electrically-insulating properties. The base body 56 includes an integral base portion 62 formed into a cylindrical block shape, a knob coupling portion 64 formed on the distal side of the base portion 62, and a tube portion 66 formed on the proximal side of the base portion 62. In this embodiment, the first vibration transmitting portion 54b of the distal side vibration transmission body 54 is disposed inside the base body 56. As shown in FIG. 2A, when the proximal side probe unit 12 and the distal side probe unit 14 are connected to each other, the proximal side vibration transmission body 24 of the proximal side probe unit 12 is disposed inside the base body 56.

The inside diameter of the base body 56 is formed to be slightly larger than the outside diameters of the first vibration transmitting portion 54b of the distal side vibration transmission body 54 of the distal side probe unit 14 and the proximal side vibration transmission body 24 of the proximal side probe unit 12. Thus, the first vibration transmitting portion 54b can rotate relative to the base body 56 around its central axis C2.

The cylindrically formed rotation knob 58 is coupled to the knob coupling portion 64 to allow a rotation operation around the central axis C2. The rotation knob 58 preferably serves as a sheath to cover the outer circumference of the second vibration transmitting portion 54c of the distal side vibration transmission body 54 in a state where the treatment portion 54d at the distal end of the distal side vibration transmission body 54 is protruding from the distal end.

The rotation knob 58 has a knob main body 72, a base body coupling portion 74 which is coupled to the knob coupling portion 64 formed on the distal side of the base portion 62, and a support portion 76 which supports the distal side vibration transmission body 54 in a whirl-stopped state.

The distal side vibration transmission body 54 is inserted through the knob main body 72, and the treatment portion 54d protrudes to the distal side from the distal end of the rotation knob 58 along the central axis C2. The outer circumferential surface of the knob main body 72 is formed as an operation portion (rotating operation portion) 72a for a user to rotate the knob 58 around the central axis C2. The inner circumferential surface at the distal end of the knob main body 72 is formed as a support portion 72b which supports the second vibration transmitting portion 54c of the distal side vibration transmission body 54 to be able to rotate or turn around the central axis C2.

The support portion 76 is formed in the inner circumferential surface of the knob main body 72 of the rotation knob 58. The support portion 76 supports the flange portion 54a of the distal side vibration transmission body 54 in a whirl-stopped state. This support position is a node position of vibration in a state where the proximal side collision portion 55 of the distal side vibration transmission body 54 abuts on the distal side collision portion 25 of the proximal side vibration transmission body 24 of the proximal side probe unit 12 and vibration is transmitted to the distal end of the distal side vibration transmission body 54 from the proximal end of the proximal side vibration transmission body 24.

If the base portion 62 of the base body 56 is held to rotate or turn the operation portion (rotation operation portion) in the outer circumferential surface of the knob main body 72 of the rotation knob 58 around the central axis C2, the proximal side vibration transmission body 24 rotates or turns around the central axis C2 together with the rotation or turning of the knob main body 72 of the rotation knob 58. That is, the distal side vibration transmission body 54 can freely rotate or turn relative to the base portion 62 and the tube portion 66 of the base body 56.

As shown in FIG. 1D, in this embodiment, balls 78 are supported on the base body coupling portion 74 at suitable intervals around the central axis C2. Friction between the knob coupling portion 64 and the base body coupling portion 74 is then reduced.

Although the balls 78 described in this embodiment are supported on the base body coupling portion 74, the balls 78 may naturally be supported on the knob coupling portion 64. That is, the balls 78 are supported between the knob coupling portion 64 and the rotation knob 58, and the balls 78 are particularly preferably supported on one of the knob coupling portion 64 and the rotation knob 58. Thus, frictional force of rotating between the knob coupling portion 64 and the rotation knob 58 is reduced.

It is not only preferable that the balls 78 are supported on the knob coupling portion 64 or the base body coupling portion 74 but also preferable that a bearing such as a thrust ball bearing which permits rotation or turning around the central axis C2 is disposed between the knob coupling portion 64 and the rotation knob 58. In addition, instead of the balls 78 or the thrust ball bearing, a lubricating sheet material or an oilless bush, for example, is preferably disposed between the knob coupling portion 64 and the rotation knob 58.

Here, for example, a press force of about 0 to 500 N is preferably generated between the knob coupling portion 64 of the base body 56 and the base body coupling portion 74 of the rotation knob 58 by the coupling of the knob coupling portion 64 and the rotation knob 58. Thus, when the distal side probe unit 14 is a single unit, the rotation knob 58 can be easily operated when rotated or turned relative to the base body 56 around the central axis C2.

As will be described later, the proximal side probe unit 12 and the distal side probe unit 14 are connected to each other, and frictional force is generated between the distal side collision portion 25 of the proximal side vibration transmission body 24 and the proximal side collision portion 55 of the distal side vibration transmission body 54. In this instance, the force necessary to rotate or turn the rotation knob 58 (difficulty of rotating or turning the rotation knob 58) can be suitably set if the frictional force between the distal side collision portion 25 and the proximal side collision portion 55 is adjusted by a later-described urging body 86.

The second connection portion 60 is formed between the proximal end of the base portion 62 of the base body 56 and the proximal end of the tube portion 66. The second connection portion 60 includes a slider 82, the cam pin 84, and the urging body 86.

An annular abutment portion (slider abutment portion) 62a which comes into abutment with the slider 82 that is urged thereto is formed at the proximal end of the base portion 62 of the base body 56. The abutment portion 62a is formed at the distal end of the tube portion 66 of the base body 56, and functions as an outward flange diametrically outwardly protruding relative to the central axis C2. An outward flange 66a diametrically outwardly protruding relative to the central axis C2 is also formed at the proximal end of the tube portion 66 of the base body 56.

The ring-shaped slider 82 is provided outside the tube portion 66 of the base body 56. The slider 82 can cooperate with the outer circumferential surface of the tube portion 66 of the base body 56 to move between the abutment portion 62a and the outward flange 66a along the central axis C2. In the meantime, the slider 82 is whirl-stopped in the outer circumference of the tube portion 66, and the rotation or turning of the slider 82 around the central axis C2 is prevented.

The cam pin 84 includes a supported portion 84a which is supported so that the supported portion 84a is prevented from coming off the slider 82, and a rotor 84b which can rotate relative to the supported portion 84a. The position of cam pin 84 does not move relative to the slider 82 in the circumferential direction, and can rotate or turn around an axis that intersects at right angles with the central axis C2. The rotor 84b is located at a position of the cam pin 84 which is diametrically distal to the central axis C2. The rotor 84b protrudes in the diametrically outward direction of the central axis C2 further than the ring-shaped slider 82 and the outward flange 66a at the proximal end of the tube portion 66.

Only one cam pin 84 may be disposed in the slider 82, but more than one cam pin 84, for example, two or three cam pins 84 are also preferable as shown in FIG. 1C. In this embodiment, as shown in FIG. 1A and FIG. 1C, a pair of cam pins 84 face the central axis C2 to be able to engage with a pair of cam grooves 34. It is also preferable for the cam pins 84 to be formed at suitable positions, for example, at positions located 90 degrees apart relative to the central axis C2.

In this embodiment, a compression coil spring is used as the urging body 86. The urging body 86 is supported between the outward flange 66a at the proximal end of the tube portion 66 and the slider 82. The urging body 86 resists a compressive force, and therefore urges the slider 82 against the abutment portion 62a of the base portion 62 on the distal side along the central axis C2 relative to the outward flange 66a.

In addition to the compression coil spring, a disc spring and a multiple disc spring, for example, can be used as the urging body 86.

An annular facing surface 62b is formed at the proximal end of the base portion 62 of the base body 56, and the distal end of the main body 26a of the exterior case 26 comes into abutment with or comes close to the facing surface 62b when the proximal side probe unit 12 is attached to the distal side probe unit 14. The facing surface 62b is formed on the further outer circumference of the abutment portion 62a.

Here, the length of the proximal side vibration transmission body 24 is adjusted so that when the distal end of the proximal side vibration transmission body 24 is in contact with the proximal end of the distal side vibration transmission body 54, this contact part (boundary) is located at an antinode position of vibration on the basis of the characteristics of the ultrasonic transducer 31. There is no stress when the boundary between the distal end of the proximal side vibration transmission body 24 and the proximal end of the distal side vibration transmission body 54 is located at the antinode position of vibration. On the contrary, vibration cannot be transmitted when the boundary between the distal end of the proximal side vibration transmission body 24 and the proximal end of the distal side vibration transmission body 54 is located at the node position of vibration. The length of the treatment portion 54d at the distal end of the distal side vibration transmission body 54 is adjusted so that the treatment portion 54d is located at the antinode position of vibration to suitably treat a living tissue.

In general, the driving frequency at which the ultrasonic transducer 31 used in the treatment instrument to treat a living tissue is driven is, for example, about 10 kHz to 100 kHz.

For example, the driving frequency of the ultrasonic transducer 31 is F, and the length of a half wavelength is λ/2. Thus, when the distal end of the proximal side vibration transmission body 24 is brought into collision with the proximal end of the distal side vibration transmission body 54 at the antinode position of vibration, the length from the distal end of the ultrasonic transducer 31 to the distal end of the proximal side vibration transmission body 24 is λ/2×n (n: an integer equal to or more than 1). Similarly, the length from the proximal end of the distal side vibration transmission body 54 to the treatment portion 54d at the distal end is λ/2×n (n: an integer equal to or more than 1). That is, the length from the ultrasonic transducer 31 to the treatment portion 54d at the distal end of the distal side vibration transmission body 54 is an integer multiple (n times) of double the half wavelength or more.

Therefore, depending on the selection of the ultrasonic transducer 31, for example, not only the proximal side vibration transmission body 24 and the distal side vibration transmission body 54 but also the length of the exterior case 26 along the central axis C1 and the length of the base body 56 along the central axis C2 change.

Here, an unshown hand switch to switch on/off the supply of energy to the ultrasonic transducer 31 is provided in an outer circumferential surface 63 of the base portion 62 of the base body 56 of the distal side probe unit 14. The hand switch may be disposed in the exterior case 26 of the proximal side probe unit 12 instead of being disposed in the base portion 62 of the base body 56 of the distal side probe unit 14.

The hand switch is preferably set so that, for example, the supply of energy to the ultrasonic transducer 31 is continued while the hand switch is being pressed, and the output of energy to the ultrasonic transducer 31 is stopped when the hand switch is released. When the supply of energy to the ultrasonic transducer 31 is switched on/off, a foot switch may be used together with or instead of the hand switch.

Next, functions of the treatment instrument 10 according to this embodiment are described.

First, the attachment of the proximal side probe unit 12 and the distal side probe unit 14 is described.

For example, the user grasps the base body 56 of the distal side probe unit 14 with the left hand, and grasps the exterior case 26 of the proximal side probe unit 12 with the right hand. The central axis C2 of the distal side probe unit 14 is aligned with the central axis C1 of the proximal side probe unit 12. The tube portion 66 of the base body 56 of the distal side probe unit 14 is received in the housing portion 26c of the proximal side probe unit 12. As indicated by a broken line in FIG. 2B, the cam pin 84 of the distal side probe unit 14 is then received in the opening 34a of the cam groove 34 of the proximal side probe unit 12. The cam pin 84 is located closer to the proximal side than the distal edge 32a of the cam ring 32 along the central axis C1. In this instance, the distal side collision portion 25 of the proximal side vibration transmission body 24 of the proximal side probe unit 12 closely faces the proximal side collision portion 55 of the distal side vibration transmission body 54 of the distal side probe unit 14.

For example, the exterior case 26 is rotated around the central axis C1 while the distal side collision portion 25 of the proximal side vibration transmission body 24 of the proximal side probe unit 12 is being brought closer to the proximal side collision portion 55 of the distal side vibration transmission body 54 of the distal side probe unit 14. In this instance, the cam pin 84 moves toward the engagement portion 34c from the opening 34a through the inclined plane 34b while sliding along the inclined plane 34b of the cam groove 34. Since each cam pin 84 can rotate around the axis that intersects at right angles with the central axis C2, the rotor 84b of the cam pin 84 moves toward the engagement portion 34c from the opening 34a while turning along the inclined plane 34b of the cam groove 34. The rotor 84b of the cam pin 84 turns in this way, so that friction is less than when the cam pin 84 is fixed to the slider 82. Thus, the friction of the inclined plane 34b of the cam groove 34 of the proximal side probe unit 12 is reduced. The rotor 84b of the cam pin 84 turns in this way so that frictional force between the cam pin 84 and the cam groove 34 is reduced. Thus, the cam pin 84 is moved toward the engagement portion 34c from the opening 34a with relatively small force.

As the cam pin 84 moves toward the engagement portion 34c from the opening 34a of the cam groove 34, the slider 82 moves toward the outward flange 66a of the tube portion 66 against the urging force of the urging body 86. After the distal side collision portion 25 of the proximal side vibration transmission body 24 of the proximal side probe unit 12 is brought into collision with the proximal side collision portion 55 of the distal side vibration transmission body 54 of the distal side probe unit 14, the cam pin 84 moves to the engagement portion 34c of the cam groove 34. Here, the distal side collision portion 25 of the proximal side vibration transmission body 24 of the proximal side probe unit 12 is in surface contact with the proximal side collision portion 55 of the distal side vibration transmission body 54 of the distal side probe unit 14.

Thus, in a state where the cam pin 84 is in engagement with the engagement portion 34c of the cam groove 34, the collision force between the distal side collision portion 25 of the proximal side vibration transmission body 24 of the proximal side probe unit 12 and the proximal side collision portion 55 of the distal side vibration transmission body 54 of the distal side probe unit 14 is adjusted by the urging body 86. Although the urging force of the urging body 86 can be suitably set, the urging force needs to be of a level that surely maintains the fitting of the exterior case 26 and the base body 56 (a state where the cam pin 84 is disposed in the engagement portion 34c of the cam groove 34) even if the exterior case 26 is held with one hand during use of the treatment instrument 10 and the base body 56 is concurrently made to suitably rotate relative to the central axes C1 and C2 with the same hand. The urging force of the urging body 86 also needs to be of a level that can satisfactorily transmit the ultrasonic vibration generated in the ultrasonic transducer 31 to the distal side vibration transmission body 54 from the proximal side vibration transmission body 24. In the meantime, the urging body 86 prevents the application of improper force equal to or more than a predetermined force between the distal side collision portion 25 of the proximal side vibration transmission body 24 of the proximal side probe unit 12 and the proximal side collision portion 55 of the distal side vibration transmission body 54 of the distal side probe unit 14.

In this way, the first connection portion 28 of the proximal side probe unit 12 is connected to the second connection portion 60 of the distal side probe unit 14. The distal end of the exterior case 26 is in collision with or close to the facing surface 62*b* at the proximal end of the base portion 62 of the base body 56 of the distal side probe unit 14.

In this instance, the distal side collision portion 25 of the proximal side vibration transmission body 24 of the proximal side probe unit 12 is kept in collision with the proximal side collision portion 55 of the distal side vibration transmission body 54 of the distal side probe unit 14. The proximal side probe unit 12 and the distal side probe unit 14 are held so that the central axes C1 and C2 are in alignment.

That is, the proximal side holding portion (proximal side cover) 22 and the distal side holding portion 52 maintain a state in which the proximal end of the distal side vibration transmission body 54 is brought into collision with the distal end of the proximal side vibration transmission body 24 so that the vibration from the ultrasonic transducer 31 can be transmitted to the distal end of the distal side vibration transmission body 54 from the proximal end of the proximal side vibration transmission body 24, and also maintain a state in which the central axes C1 and C2 are in alignment.

In this state, the hand switch is pressed to supply energy to the ultrasonic transducer 31 at the proximal end of the proximal side vibration transmission body 24 through the electric power supply cords 31*a* and 31*b* and thereby generate vibration. Thus, the ultrasonic vibration is transmitted to the treatment portion 54*d* at the distal end of the distal side vibration transmission body 54 from the proximal end of the proximal side vibration transmission body 24. A living tissue, for example, is then suitably treated by the treatment portion 54*d* at the distal end of the distal side vibration transmission body 54.

The distal side collision portion 25 of the proximal side vibration transmission body 24 of the proximal side probe unit 12 and the proximal side collision portion 55 of the distal side vibration transmission body 54 of the distal side probe unit 14 are located at positions other than the node positions of vibration, and are particularly preferably located at the antinode positions of vibration where there is no stress when the ultrasonic vibration is transmitted to the proximal side collision portion 55 of the distal side vibration transmission body 54 from the distal side collision portion 25 of the proximal side vibration transmission body 24.

When the direction of the treatment portion 54*d* is changed, the rotation knob 58 of the distal side probe unit 14 is grasped and then rotated around the central axes C1 and C2 while the exterior case 26 of the proximal side probe unit 12 is grasped with, for example, the right hand. No turning force is applied to the base body 56 by the right hand and the left hand.

The rotation knob 58 can be rotated relative to the proximal side probe unit 12 and the base body 56 around the central axis C2 in two directions here, but can be rotated in any direction.

In response to the rotation of the rotation knob 58, the distal side vibration transmission body 54 which is whirl-stopped on the rotation knob 58 rotates around the central axis C2 together with the rotation knob 58. The friction between the rotation knob 58 and the base body 56 is reduced by, for example, the balls 78. Thus, the base body 56 does not turn together with the rotation knob 58. The proximal side vibration transmission body 24 which is whirl-stopped on the exterior case 26 remains as it is together with the ultrasonic transducer unit 30.

The distal side collision portion 25 of the proximal side vibration transmission body 24 of the proximal side probe unit 12 and the proximal side collision portion 55 of the distal side vibration transmission body 54 of the distal side probe unit 14 rotate around the central axes C1 and C2 while sliding on each other. In this way, the distal side vibration transmission body 54 rotates around its central axis C2, and the direction of the treatment portion 54*d* is changed relative to the proximal side vibration transmission body 24 and the ultrasonic transducer unit 30. Thus, the treatment instrument 10 according to this embodiment can adjust the direction of the treatment portion 54*d* without moving the proximal side vibration transmission body 24, the exterior case 26, and the ultrasonic transducer unit 30. Therefore, the direction of the treatment portion 54*d* can be changed to a desired direction for the user without changing the position of the hand switch disposed in the outer circumferential surface 63 of the base portion 62 of the base body 56.

The operation to change the direction of the treatment portion 54*d* may be performed with either one hand or both hands. For example, the rotation knob 58 of the distal side probe unit 14 may be grasped with the left hand, and the exterior case 26 of the proximal side probe unit 12 may be grasped with the right hand, and the left hand may be moved to rotate the rotation knob 58 relative to the exterior case 26 with respect to the central axes C1 and C2.

When the distal side probe unit 14 is detached from the proximal side probe unit 12, for example, the base body 56 (and the rotation knob 58) of the distal side probe unit 14 is grasped with the left hand, and the exterior case 26 of the proximal side probe unit 12 is grasped with the right hand. In this state, the proximal side probe unit 12 and the distal side probe unit 14 are rotated relative to each other to the side opposite to that in the case where the distal side probe unit 14 is attached to the proximal side probe unit 12. That is, force is applied such that the base body 56 of the distal side probe unit 14 in the left hand and the exterior case 26 of the proximal side probe unit 12 in the right hand cannot be moved with one hand in the opposite directions around the central axes C1 and C2.

The cam pin 84 is disposed in the inclined plane 34*b* over the movement regulation portion 34*d* from the engagement portion 34*c* of the cam groove 34, and then removed. In this instance, the slider 82 is urged toward the distal side along the central axis C2 by the urging body 86, so that the rotor 84*b* of the cam pin 84 slides on the inclined plane 34*b* of the cam groove 34 toward the opening 34*a* while rotating around its axis. Thus, the distal side collision portion 25 of the proximal side vibration transmission body 24 of the proximal side probe unit 12 and the proximal side collision portion 55 of the distal side vibration transmission body 54 of the distal side probe unit 14 are brought out of collision. The cam pin 84 is then taken out of the opening 34*a* of the cam groove 34.

The proximal side probe unit 12 is then moved to the proximal side along the central axis C1, and the distal side probe unit 14 is moved to the distal side along the central axis C2, so that the proximal side probe unit 12 and the distal side probe unit 14 are separated from each other. Thus, the tube portion 66 of the base body 56 of the distal side probe unit 14 is taken out of the housing portion 26*c* of the proximal side probe unit 12. In this way, the first connection portion 28 of the proximal side probe unit 12 is disconnected from the second connection portion 60 of the distal side probe unit 14.

For example, when the distal side probe unit 14 having a differently shaped treatment portion 54d is used, the distal side probe unit 14 is attached to the proximal side probe unit 12 as described above.

The proximal side probe unit 12 is preferably cleaned, disinfected, and sterilized, and then reused. The distal side probe unit 14 is disposed of as it is. The distal side probe unit 14 may also be cleaned, disinfected, and sterilized, and then reused.

As described above, the following can be said according to the treatment instrument 10 in this embodiment.

If the exterior case 26 of the proximal side probe unit 12 and the base body 56 of the distal side probe unit 14 are grasped and relatively rotated in the opposite directions around the central axes C1 and C2, the first connection portion 28 of the proximal side probe unit 12 can be connected to or disconnected from the second connection portion 60 of the distal side probe unit 14. That is, the first and second connection portions 28 and 60 cooperate to constitute an attachment/detachment mechanism between the proximal side probe unit 12 and the distal side probe unit 14. Such an attachment/detachment mechanism 28 and 60 can attach and detach the first and second holding portions 22 and 52 to and from each other by relatively turning or rotating the first and second holding portions 22 and 52 around the central axes C1 and C2.

Thus, no exclusive tool is needed to connect, that is, attach or disconnect, that is, detach the proximal side probe unit 12 and the distal side probe unit 14. Therefore, it is possible to easily perform an operation to replace the distal side probe unit 14 having the treatment portion 54d for the proximal side probe unit 12.

When the direction of the treatment portion 54d is to be changed after the proximal side probe unit 12 and the distal side probe unit 14 are connected, it is possible to rotate or turn the distal side vibration transmission body 54 having the treatment portion 54d at the distal end around the central axes C1 and C2 without moving the proximal side vibration transmission body 24 having the ultrasonic transducer unit 30 disposed at the proximal end. Thus, during use of the treatment instrument 10, it is possible to prevent a load from being applied to the ultrasonic transducer unit 30, and also change the direction of the treatment portion 54d to a suitable direction.

In this instance, by the action of the urging body 86, the distal side collision portion 25 of the proximal side vibration transmission body 24 and the proximal side collision portion 55 of the distal side vibration transmission body 54 are in close contact with each other with suitable pressure that permits the transmission of ultrasonic vibration. Thus, when vibration is generated in the ultrasonic transducer 31, it is possible to maintain a vibration transmitting performance similar to that in the case where the distal side collision portion 25 of the proximal side vibration transmission body 24 is screwed to the proximal side collision portion 55 of the distal side vibration transmission body 54.

For example, the balls 78 allow the rotation knob 58 of the distal side probe unit 14 to be easily rotated or turned relative to the base body 56 by the force of the finger of the user. In this instance, the distal side collision portion 25 of the proximal side vibration transmission body 24 of the proximal side probe unit 12 and the proximal side collision portion 55 of the distal side vibration transmission body 54 of the distal side probe unit 14 are in collision with each other so that the collision force is adjusted by the urging body 86. Thus, the friction between the distal side collision portion 25 of the proximal side vibration transmission body 24 of the proximal side probe unit 12 and the proximal side collision portion 55 of the distal side vibration transmission body 54 of the distal side probe unit 14 prevents the rotation knob 58 on which the distal side vibration transmission body 54 is whirl-stopped from automatically rotating or turning relative to the base body 56. It is therefore possible to direct the treatment portion 54d in a desired direction after applying suitable force to the rotation knob 58 while maintaining the positions of the ultrasonic transducer unit 30 and the proximal side vibration transmission body 24.

To transmit the ultrasonic vibration from the proximal side vibration transmission body 24 to the distal side vibration transmission body 54, great force is applied by the urging body 86 when the distal end of the proximal side vibration transmission body 24 is brought into collision with the distal end of the distal side vibration transmission body 54. The cam pin 84 according to this embodiment moves while rotating when moving toward the engagement portion 34c from the opening 34a of the cam groove 34. Thus, greater force is applied to the urging body 86, but a relatively small force can be applied to connect the proximal side probe unit 12 and the distal side probe unit 14.

High-frequency energy can be input to the proximal side probe unit 12 by a known mechanism together with or instead of ultrasonic vibration. Thus, although the treatment instrument 10 to treat a living tissue using ultrasonic vibration has been described by way of example in this embodiment, it is also possible to use, for example, high-frequency energy together with or instead of ultrasonic vibration. These energies are switched by, for example, the hand switch and the foot switch.

The following gives further details of the distal side probe unit 14 of the treatment instrument 10 according to this embodiment.

The distal side probe unit 14 of the treatment instrument 10 includes the distal side holding portion 52 and the second vibration transmission body (distal side probe) 54. The distal side holding portion 52 is attachable to and detachable from the exterior case (proximal side holding portion) 26 to hold the first vibration transmission body (proximal side probe) 24 which defines the first central axis C1 and which transmits the ultrasonic vibration from the ultrasonic transducer 31 from its proximal end to its distal end along the first central axis C1. The distal side vibration transmission body 54 is held to the distal side holding portion 52, defines the second central axis C2, and can transmit ultrasonic vibration from its proximal end to the treatment portion 54d at the distal end along the second central axis C2. The distal side vibration transmission body 54 can transmit ultrasonic vibration from the ultrasonic transducer 31 from the proximal end of the proximal side vibration transmission body 24 to the treatment portion 54d at its distal end in a state where the distal side collision portion 25 at the distal end of the proximal side vibration transmission body 24 is in collision with the proximal side collision portion 55 at its proximal end and the distal side collision portion 25 of the proximal side vibration transmission body 24 is in collision with the proximal side collision portion 55 while the first and second central axes C1 and C2 are in alignment when the distal side holding portion 52 and the proximal side holding portion 22 are attached. The distal side vibration transmission body 54 can turn or rotate relative to the proximal side vibration transmission body 24 around the first and second central axes C1 and C2 to direct the treatment portion 54d at the distal end in a desired direction.

The distal side holding portion 52 includes the rotation knob (operation portion) 58 which turns or rotates the second vibration transmission body (distal side probe) 54 relative to the first vibration transmission body (proximal side probe) 24 around the second central axis C2 of the distal side holding portion 52 by an operation to rotate around the second central axis C2.

The following gives further details of the proximal side probe unit 12 of the treatment instrument 10 according to this embodiment.

The proximal side probe unit 12 of the treatment instrument 10 has the proximal side holding portion (proximal side cover) 22 and the first vibration transmission body (proximal side probe) 24. The proximal side holding portion 22 is attachable to and detachable from the distal side holding portion 52 to hold the second vibration transmission body (distal side probe) 54 which defines the second central axis C2 and which can transmit ultrasonic vibration from its proximal end to the treatment portion 54d at the distal end along the second central axis C2. The proximal side vibration transmission body 24 is held to the proximal side holding portion 22, and defines the first central axis C1, and transmits ultrasonic vibration from the ultrasonic transducer 31 to the proximal side vibration transmission body 24 from its proximal end to its distal end along the first central axis C1. The proximal side vibration transmission body 24 can transmit ultrasonic vibration from the ultrasonic transducer 31 from its proximal end of the treatment portion 54d at the distal end of the distal side vibration transmission body 54 in a state where the central axes C1 and C2 are in alignment, the distal side collision portion 25 at the distal end is brought into collision with the proximal side collision portion 55 at the proximal end of the distal side vibration transmission body 54, and the proximal side collision portion 55 of the distal side vibration transmission body 54 is in collision with the distal side collision portion 25 at the distal end when the proximal side holding portion 22 is attached to the distal side holding portion 52. The proximal side vibration transmission body 24 can turn or rotate relative to the distal side vibration transmission body 54 around the first and second central axes C1 and C2 to direct the treatment portion 54d at the distal end of the distal side vibration transmission body 54 in a desired direction.

The following gives further details of the treatment instrument 10 according to this embodiment.

The treatment instrument 10 includes the first vibration transmission body (proximal side probe) 24, the second vibration transmission body (distal side probe) 54, the holding portion (the proximal side holding portion (proximal side cover) 22 and the distal side holding portion 52), and the rotation knob (operation portion) 58. The first vibration transmission body (proximal side probe) 24 extends along the first central axis C1 defined by its proximal end and its distal end, and transmits ultrasonic vibration from the ultrasonic transducer 31 from its proximal end to its distal end along the first central axis C1. The second vibration transmission body (distal side probe) 54 extends along the second central axis C2 defined by its proximal end and its distal end, and can transmit ultrasonic vibration from its proximal end to the treatment portion 54d at the distal end along the second central axis C2. The holding portion maintains a state in which the proximal side collision portion 55 of the distal side vibration transmission body 54 is in collision with the distal side collision portion 25 of the proximal side vibration transmission body 24 so that vibration from the ultrasonic transducer 31 can be transmitted to the distal end of the distal side vibration transmission body 54 from the proximal end of the proximal side vibration transmission body 24, and also maintains a state in which the first and second central axes C1 and C2 are in alignment. The rotation knob 58 is provided in the holding portion, and can turn or rotate the distal side vibration transmission body 54 relative to the proximal side vibration transmission body 24 around the first and second central axes C1 and C2 by an operation to rotate around the first and second central axes C1 and C2, to direct the treatment portion 54d at the distal end of the distal side vibration transmission body 54 in a desired direction.

The holding portion (distal side holding portion) 52 includes the urging body 86 which presses the distal end of the proximal side vibration transmission body (proximal side probe) 24 and the proximal end of the second vibration transmission body (distal side probe) 54 with a constant force.

The attachment/detachment mechanism is provided, and attaches the proximal side holding portion (proximal side cover) 22 and the distal side holding portion 52 to each other while bringing the distal end of the proximal side vibration transmission body (proximal side probe) 24 and the proximal end of the distal side vibration transmission body (distal side probe) 54 into collision with each other, and detaches the proximal side holding portion (proximal side cover) 22 and the distal side holding portion 52 from each other while bringing the distal end of the proximal side vibration transmission body 24 and the proximal end of the distal side vibration transmission body 54 out of collision with each other.

Next, a first modification of the first embodiment is described with reference to FIG. 3.

In the example described in this embodiment, the titanium alloy rod integral with the horn 30b and the flange portion 30a of the ultrasonic transducer unit 30 is used as the proximal side vibration transmission body 24 as shown in FIG. 1A. In the example described in this modification, the horn 30b and the flange portion 30a of the ultrasonic transducer unit 30 at the proximal end of the proximal side vibration transmission body 24 are formed not integrally with but separately from the proximal side vibration transmission body 24.

Figure 3:
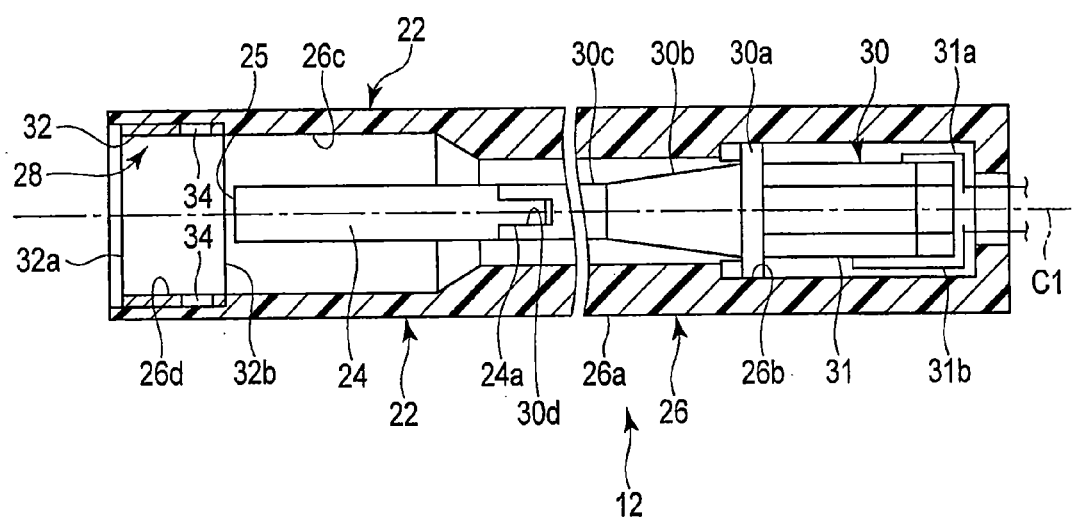
FIG. 3 is a schematic longitudinal sectional view showing the proximal side probe unit of a treatment instrument according to a first modification of the first embodiment.

As shown in FIG. 3, the ultrasonic transducer unit 30 includes a vibration transmitting portion 30c which transmits the vibration whose amplitude has been increased by the horn 30b. An internal thread 30d is formed at the distal end of the vibration transmitting portion 30c, an external thread 24a is formed at the proximal end of the proximal side vibration transmission body 24, and these threads are coupled to each other.

In the example described in the first embodiment, the ultrasonic transducer 31 is directly disposed at the proximal end of the proximal side vibration transmission body 24 via the horn 30b and the flange portion 30a integral with the proximal side vibration transmission body 24. In contrast, it is also preferable that the vibration transmitting portion 30c is screwed to the proximal end of the proximal side vibration transmission body 24, and the ultrasonic transducer unit 30, that is, the horn 30b and the flange portion 30a are integrated with the vibration transmitting portion 30c. In other words, it is also preferable that the proximal end of the proximal side vibration transmission body 24 is coupled to the distal end of an ultrasonic probe formed by the vibration transmitting portion 30c, the horn 30b, and the flange portion 30a. In this case, the length from the ultrasonic transducer 31 to the distal end of the vibration transmitting portion 30c is formed to be the length of an integer multiple of the length of a half wavelength. Thus, the proximal end of the proximal side vibration transmission body 24 is coupled to the distal end of the vibration transmitting portion 30c of the ultrasonic transducer unit 30 at the antinode positions of vibration.

Therefore, the ultrasonic transducer unit 30 may be integrally formed or detachably formed as a separate unit at the proximal end of the proximal side vibration transmission body 24.

Although the proximal side holding portion 22 holds the proximal side vibration transmission body 24 in the explanation according to the first embodiment, the proximal side holding portion 22 does not always need to hold the proximal side vibration transmission body 24, and the proximal side vibration transmission body (proximal side probe) 24 has only to be disposed inside. That is, the proximal side holding portion 22 is used as a proximal side cover. This applies not only to modifications described below but also to the second to fourth embodiments.

Figure 4:
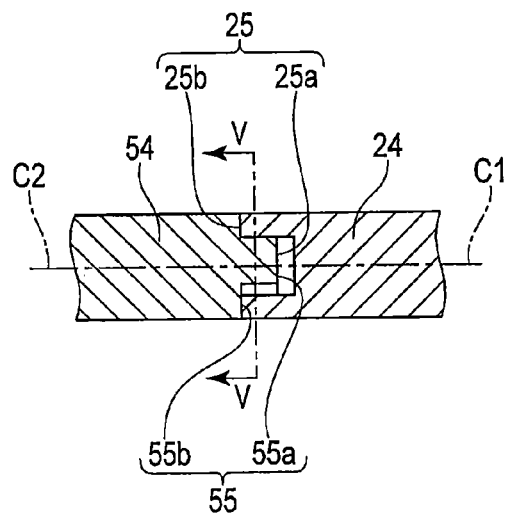
FIG. 4 is a schematic longitudinal sectional view showing a state where a distal side collision portion of a proximal side vibration transmission body of the treatment instrument according to a second modification of the first embodiment is in collision with a proximal side collision portion of a distal side vibration transmission body.

Next, a second modification of the first embodiment is described with reference to FIG. 4 to FIG. 5C.

In FIG. 1A, the distal side collision portion 25 of the proximal side vibration transmission body 24 and the proximal side collision portion 55 of the distal side vibration transmission body 54 are shown as the planes that intersect at right angles with the central axes C1 and C2. As shown in FIG. 4, it is also preferable that, for example, a recess 25a and a circular surface (distal surface) 25b are formed in the distal side collision portion 25 of the proximal side vibration transmission body 24, a protrusion 55a and a circular surface (proximal surface) 55b are formed in the proximal side collision portion 55 of the distal side vibration transmission body 54, and the recess 25a and the protrusion 55a can be fitted together in a state where the circular surfaces 25b and 55b are in collision with each other. When the circular surfaces 25b and 55b are in collision with each other, vibration generated in the ultrasonic transducer 31 can be transmitted to the distal side vibration transmission body 54 from the proximal side vibration transmission body 24 through the circular surfaces 25b and 55b.

In the example shown in FIG. 5A, the recess 25a of the distal side collision portion 25 of the proximal side vibration transmission body 24 is formed as a circular columnar space. The protrusion 55a of the proximal side collision portion 55 of the distal side vibration transmission body 54 has three integral circular-arc surfaces 92a formed at equal intervals of, for example, 60 degrees relative to the central axis C2, and recessed surfaces 92b formed between the circular-arc surfaces 92a. The surfaces forming the recessed surfaces 92b are located closer to the central axis C2 than the circular-arc surfaces 92a. The height of the protrusion 55a along the central axis C2 relative to the circular surface (proximal surface) 55b is smaller than the depth of the recess 25a along the central axis C1 relative to the circular surface (distal surface) 25b. Thus, the circular surface (distal surface) 25b around the recess 25a and the circular surface (proximal surface) 55b around the protrusion 55a come into close contact with each other in an engagement state.

The inner circumferential surface of the circular columnar recess 25a and the three circular-arc surfaces 92a are formed to be able to rotate or turn relative to one another in surface contact. In this instance, the central axes C1 and C2 can be kept in alignment by the relation between the recess 25a and the protrusion 55a during sliding and rotating or turning around the central axes C1 and C2.

The central axes C1 and C2 can also be aligned when the distal side collision portion 25 of the proximal side vibration transmission body 24 is brought into collision with the proximal side collision portion 55 of the distal side vibration transmission body 54. Thus, the shift of the central axes C1 and C2 can be prevented.

As long as the proximal side of the protrusion 55a along the central axis C2 is a taper inclined plane and the position close to the circular surface 55b is formed as shown in FIG. 5A, the central axes C1 and C2 can be more easily aligned when the recess 25a and the protrusion 55a are fitted together.

In the example shown in FIG. 5B, the protrusion 55a of the proximal side collision portion 55 of the distal side vibration transmission body 54 includes three integral circular arcs 94a, and three projections 94b formed at equal intervals of, for example, 120 degrees relative to the central axis C2. The three circular arcs 94a are located apart from the inner circumferential surface of the recess 25a of the distal side collision portion 25 of the proximal side vibration transmission body 24. Each of the projections 94b is formed between the circular arcs 94a. The distal end of each of the projections 94b is located more distal to the central axis C2 than the circular arcs 94a, and can slide on the inner circumferential surface of the recess 25a. That is, the inner circumferential surface of the circular columnar recess 25a and the three projections 94b are formed to be able to rotate or turn relative to each another. Even if the protrusion 55a is formed into the state shown in FIG. 5B, the central axes C1 and C2 can be kept in alignment by the relation between the recess 25a and the protrusion 55a during sliding and rotating or turning around the central axes C1 and C2 as in the example shown in FIG. 5A. The three projections 94b may be in line contact or point contact with the inner circumferential surface of the circular columnar recess 25a. When in line contact, each of the projections 94b extends in parallel with the central axis C2.

In the example shown in FIG. 5C, the protrusion 55a of the proximal side collision portion 55 of the distal side vibration transmission body 54 is formed into a circular columnar shape. On the other hand, three projections 96 which diametrically inwardly protrude toward the central axis C1 and which can abut on the outer circumferential surface of the protrusion 55a are formed in the recess 25a. Even if the protrusion 55a is formed in the state shown in FIG. 5C, the central axes C1 and C2 can be kept in alignment by the relation between the recess 25a and the protrusion 55a during sliding and rotating or turning around the central axes C1 and C2, as in the example shown in FIG. 5A. The three projections 96 may be in line contact or point contact with the outer circumferential surface of the protrusion 55a. When in line contact, each of the projections 96 extends in parallel with the central axis C1.

The distal side collision portion 25 of the proximal side vibration transmission body 24 and the proximal side collision portion 55 of the distal side vibration transmission body 54 in FIG. 5A to FIG. 5C can align the central axes C1 and C2 when brought into collision with each other. When the distal side collision portion 25 of the proximal side vibration transmission body 24 and the proximal side collision portion 55 of the distal side vibration transmission body 54 rotate around the central axes C1 and C2, the central axes C1 and C2 can be kept in alignment.

Next, a third modification of the first embodiment is described with reference to FIG. 6A to FIG. 6C.

In the first embodiment, the proximal side vibration transmission body 24 and the distal side vibration transmission body 54 use the same material. Alternatively, it is also preferable if the material of the proximal side vibration transmission body 24 and the distal side vibration transmission body 54 is suitably changed so that the distal side collision portion 25 of the proximal side vibration transmission body 24 is formed to be more hard-wearing than the proximal side collision portion 55 of the distal side vibration transmission body 54. The distal side collision portion 25 of the proximal side vibration transmission body 24 is formed to be more hard-wearing than the proximal side collision portion 55 of the distal side vibration transmission body 54 because the probability of reuse of the proximal side probe unit 12 is higher than the probability of reuse of the distal side probe unit 14.

As shown in FIG. 6A, the distal side vibration transmission body 54 of the distal side probe unit 14 may be formed by two bodies instead of one body. The distal side vibration transmission body 54 includes a proximal side vibration transmitting portion (first transmitting portion) 154a and a distal side vibration transmitting portion (second transmitting portion) 154b from the proximal side to the distal side along the central axis C2. An internal thread 155a is formed at the distal end of the proximal side vibration transmitting portion 154a, an external thread 155b is formed at the proximal end of the distal side vibration transmitting portion 154b, and these threads are coupled to each other. That is, the distal side vibration transmission body 54 has two rod-shaped members that are coupled to each other along the central axis C2 by the threads 155a and 155b as coupling portions 155.

The coupling portion of the distal end of the proximal side vibration transmitting portion 154a and the proximal end of the distal side vibration transmitting portion 154b corresponds to the antinode position of vibration.

The proximal side vibration transmitting portion 154a of the distal side vibration transmission body 54 is made of a material which is softer and lower in Young's modulus than the proximal side vibration transmission body 24. Specifically, a titanium alloy material such as 6-4 Ti is used for the proximal side vibration transmission body 24 and the distal side vibration transmitting portion 154b of the distal side vibration transmission body 54, and an aluminum alloy material is used for the proximal side vibration transmitting portion 154a of the distal side vibration transmission body 54.

Here, in the example of the operation described in the first embodiment, as shown in FIG. 2A, the distal side collision portion 25 of the proximal side vibration transmission body 24 made of the titanium alloy material and the proximal side collision portion 55 of the distal side vibration transmission body 54 made of the same titanium alloy material are directly brought into collision with each other to change the direction of the treatment portion 54d of the distal side vibration transmission body 54 relative to the proximal side vibration transmission body 24. Here, as shown in FIG. 6A, it is possible to perform an operation to bring the proximal side collision portion 55 of the proximal side vibration transmitting portion 154a of the distal side vibration transmission body 54 made of the aluminum alloy material into collision with the distal side collision portion 25 of the proximal side vibration transmission body 24 made of the titanium alloy material to change the direction of the treatment portion 54d of the distal side vibration transmission body 54 relative to the proximal side vibration transmission body 24. In this case, the distance from the ultrasonic transducer unit 30 to the treatment portion 54d can be suitably increased. The proximal side collision portion 55 of the proximal side vibration transmitting portion 154a of the distal side vibration transmission body 54 made of the aluminum alloy material is softer and lower in Young's modulus than the distal side collision portion 25 of the proximal side vibration transmission body 24 made of the titanium alloy material, so that deterioration such as abrasion of the distal side collision portion 25 of the proximal side vibration transmission body 24 can be prevented. It is therefore possible to prolong the life of the proximal side probe unit 12.

The proximal side collision portion 55 is softer than the distal side collision portion 25, so that when the distal side collision portion 25 is brought into collision with the proximal side collision portion 55, the distal side collision portion 25 can be more easily brought into close contact with the proximal side collision portion 55 than in the case where the proximal side collision portion 55 and the distal side collision portion 25 are made of the same material. Thus, when the distal side collision portion 25 is brought into collision with the proximal side collision portion 55, the performance of the close contact therebetween can be improved. Accordingly, the amount of force needed to keep the distal side collision portion 25 in collision with the proximal side collision portion 55 can be smaller than in the case where the distal side collision portion 25 and the proximal side collision portion 55 are made of the same material. Consequently, by the adjustment of the urging body 86, the force amounts to couple and decouple the proximal side probe unit 12 and the distal side probe unit 14 can be smaller than in the case described in the first embodiment.

In the distal side vibration transmission body 54, a stainless steel material may be used for the proximal side vibration transmitting portion 154a, and a titanium alloy material may be used for the distal side vibration transmitting portion 154b. Even when these materials are suitably used, the distal side vibration transmission body 54 can be used as in the state shown in FIG. 6A.

Furthermore, in the distal side vibration transmission body 54, an aluminum alloy material may be used for the proximal side vibration transmitting portion 154a, and a stainless steel material may be used for the distal side vibration transmitting portion 154b. Even when these materials are suitably used, the distal side vibration transmission body 54 can be used as in the state shown in FIG. 6A.

The proximal side vibration transmitting portion 154a of the distal side vibration transmission body 54 shown in FIG. 6B is formed to be much shorter than the proximal side vibration transmitting portion 154a of the distal side vibration transmission body 54 shown in FIG. 6A. The proximal side vibration transmitting portion 154a shown in FIG. 6B may be, for example, about several millimeters. In this case, the proximal side collision portion 55 and the coupling portions 155 of the proximal side vibration transmitting portion 154a are each located at the antinode position of vibration. In this case, no node position of vibration is present between the proximal side collision portion 55 and the coupling portions 155.

The structure shown in FIG. 6B is preferably used when the length from the ultrasonic transducer 31 to the treatment portion 54d is reduced to increase amplitude and when vibration with greater amplitude than in the structure shown in FIG. 6A is required.

Between the distal end of the proximal side vibration transmission body 24 and the proximal end of the distal side vibration transmission body 54 shown in FIG. 6C, an intermediate member 157 which is attachable to and detachable from both the transmission bodies is disposed. That is, the distal side collision portion 25 and the proximal side collision portion 55 may be brought into direct collision or may be brought into indirect collision via the intermediate member 157.

The intermediate member 157 includes a proximal side recess 157a into which the distal side collision portion 25 fits through collision, and a distal side recess 157b into which the proximal side collision portion 55 fits through collision.

A material which is softer than the proximal side vibration transmission body 24 and which has satisfactory acoustic characteristics (a material that easily transmits vibration) is used for the intermediate member 157. When the proximal side vibration transmission body 24 is made of a titanium alloy material, an aluminum alloy material, for example, is used for the intermediate member 157.

The intermediate member 157 is fitted to the distal end of the proximal side vibration transmission body 24 and the proximal end of the distal side vibration transmission body 54. The length of the intermediate member 157 along the central axes C1 and C2 (the length that contributes to vibration transmission) has only to be, for example, about several millimeters.

The intermediate member 157 is attached to the part between the distal end of the proximal side vibration transmission body 24 and the proximal end of the distal side vibration transmission body 54, for example, by the urging force of the urging body 86 when the proximal side probe unit 12 is attached to the distal side probe unit 14. When the direction of the treatment portion 54d is changed around the central axis C2, the intermediate member 157 may turn together with the distal side vibration transmission body 54, and maintain its position together with the proximal side vibration transmission body 24.

In addition, the distal side collision portion 25 of the proximal side vibration transmission body 24 of the proximal side probe unit 12 described in the first embodiment may be subjected to a surface coating treatment. Even when the proximal side vibration transmission body 24 and the distal side vibration transmission body 54 are made of the same material (e.g., a titanium alloy material), it is possible to prevent the abrasion of the distal side collision portion 25 of the proximal side vibration transmission body 24 by a surface coating treatment such as a nitriding treatment or ceramic spraying.

It is possible to use not only a titanium alloy material but also an aluminum alloy material having satisfactory acoustic characteristics for the proximal side vibration transmission body 24 of the proximal side probe unit 12. When an aluminum alloy material is used for the proximal side vibration transmission body 24, it is preferable to subject the distal side collision portion 25 to a surface treatment such as a hardened alumite treatment or ceramic spraying.

If the proximal side vibration transmission body 24 in which the distal side collision portion 25 is subjected to such a surface treatment is used, it is possible to prevent the deterioration of a titanium alloy material or an aluminum alloy material which is strong enough when used in a living tissue and which has satisfactory acoustic characteristics, and prolong the life.

Next, a fourth modification of the first embodiment is described with reference to FIG. 7 to FIG. 8B.

Figure 7:
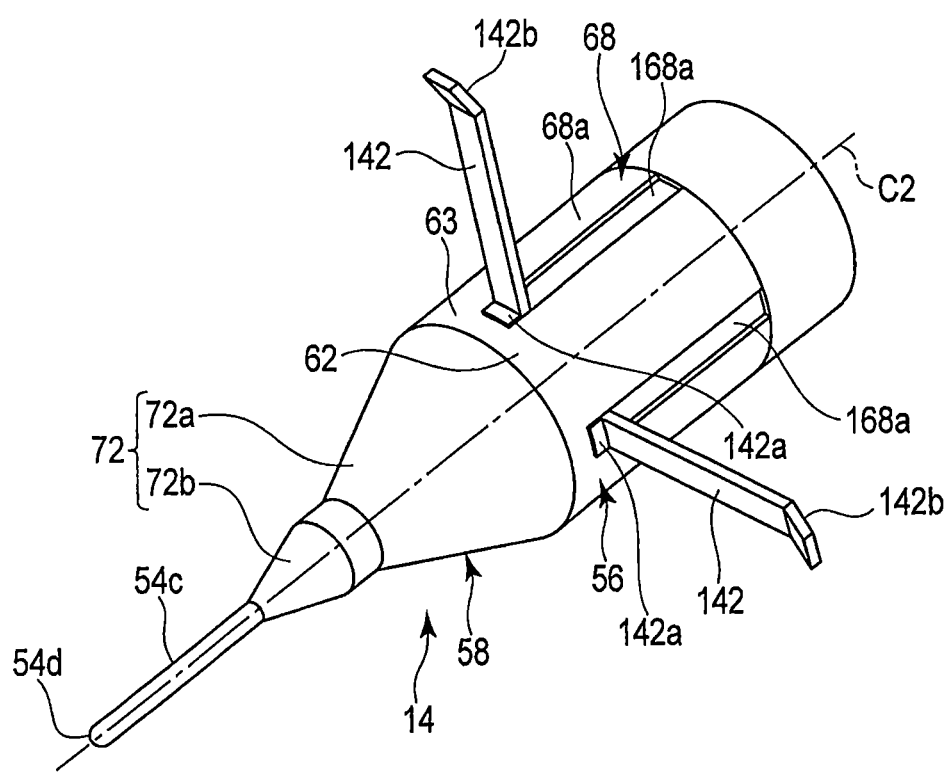
FIG. 7 is a schematic perspective view showing the distal side probe unit of the treatment instrument according to a fourth modification of the first embodiment.
Figure 8A:
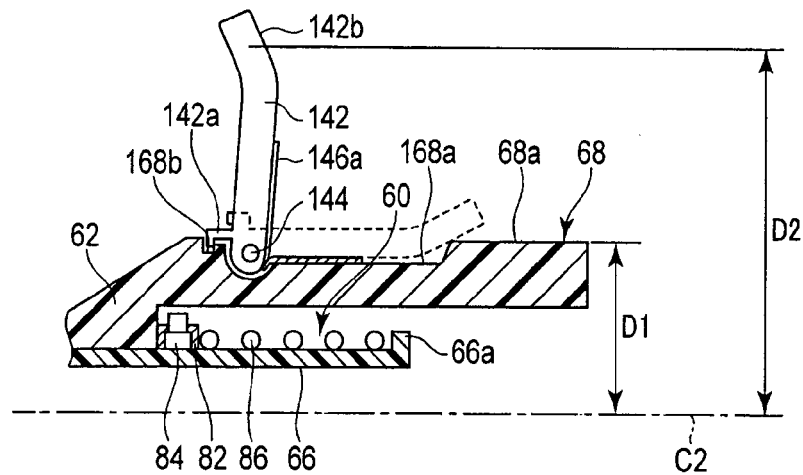
FIG. 8A is a schematic longitudinal sectional view showing a state where the distal end of a movable lever disposed outside a cylindrical body of a base body of the distal side probe unit of the treatment instrument according to the fourth modification of the first embodiment is brought away from the cylindrical body.

As shown in FIG. 7 and FIG. 8A, in this modification, the base body 56 includes a cylindrical body 68 covering the second connection portion 60 continuously with the base portion 62 on the proximal side relative to its central axis C2.

One or more movable levers (rotating torque applying portions) 142 are disposed in the outer circumferential surface of the cylindrical body 68 of the base body 56 rotatably on pivot shafts 144 that intersect at right angles with the central axis C2. Thus, later-described distal ends 142b of the movable levers 142 can increase and decrease the outside diameter by the pivot shafts 144. The movable levers (movable portions) 142 are used to attach and detach the proximal side probe unit 12 and the distal side probe unit 14. The movable levers 142 are preferably made of, for example, a stainless steel material having rigidity because a load is applied to the movable levers 142 when the distal side probe unit 14 is attached to and detached from the proximal side probe unit 12.

Housing portions 168a which house the movable levers 142 and which preferably have longitudinal axes, for example, parallel to the central axis C2, and engagement recesses 168b with which engagement protrusions 142a of the movable levers 142 are engaged are formed in an outer circumferential surface 68a of the cylindrical body 68 of the base body 56. In the movable levers 142, torsion springs (movable portions) 146a are disposed on the pivot shafts (movable portions) 144. The torsion springs 146a urge the movable levers 142 toward the housing portions 168a so that the movable levers 142 are housed in the housing portions 168a. This prevents the movable levers 142 from suddenly opening outward during a treatment using ultrasonic vibration or prevents the movable levers 142 of the distal side probe unit 14 from shutting off the view of the user as much as possible.

For example, when the proximal side probe unit 12 and the distal side probe unit 14 are attached to each other, the movable levers 142 are rotated around the pivot shafts 144 against the urging force of the torsion spring 146a. That is, as indicated by a solid line in FIG. 8A, the movable levers 142 are rotated and raised. In this instance, the engagement protrusions 142a of the movable levers 142 are engaged with the engagement recesses 168b of the cylindrical body 68. Consequently, the movable levers 142 can be kept raised.

Thus, when the movable levers 142 are kept raised, a distance D1 between the central axis C2 and the outer circumferential surface 68a of the cylindrical body 68 of the base body 56, and a distance D2 between the central axis C2 and the distal end 142b to the pivot shaft 144 in a state where the movable levers 142 are raised to the fullest agree with D1<D2.

Thus, more torque can be applied to the base body 56 when the user grasps the movable levers 142 to turn the base body 56 around the central axis C2 than when the user grasps the outer circumferential surface of the cylindrical body 68 to turn the base body 56 around the central axis C2. Therefore, in the case where the user attaches to a part between the proximal side probe unit 12 and the distal side probe unit 14, the load on the user can be less when the user grasps the distal ends 142b of the raised movable levers 142 and rotates around the central axis C2 than when the user grasps the outer circumferential surface 68a of the base body 56 to rotate the distal side probe unit 14 and rotates around the central axis C2. Such use of the movable levers 142 can reduce the load on the user when the proximal side probe unit 12 and the distal side probe unit 14 are attached to and detached from each other against the urging force of the urging body 86.

If the distal ends 142b of the movable levers 142 are caught in and engaged with the engagement recesses 168b in a state where the movable levers 142 are raised to the fullest, the positions of the movable levers 142 can be held. Thus, the user can easily rotate the distal ends 142b of the raised movable levers 142 around the central axis C2.

Figure 8B:
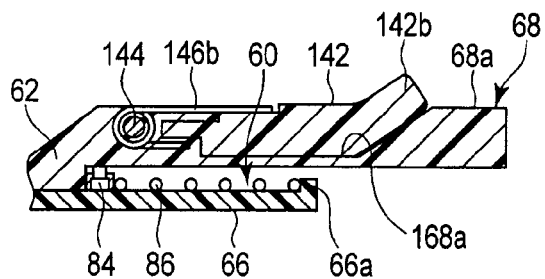
FIG. 8B is a schematic longitudinal sectional view showing a state where the distal end of the movable lever disposed outside the cylindrical body of the base body of the distal side probe unit of the treatment instrument according to a further modification of the fourth modification of the first embodiment is brought close to the cylindrical body.

FIG. 8B shows the relation between the movable lever 142 and a torsion spring (movable portion) 146b different from the relation between the movable lever 142 and the torsion spring 146a in FIG. 8A. The torsion spring 146a shown in FIG. 8A pulls the movable lever 142 to the housing portion 168a by urging. In contrast, the torsion spring 146b shown in FIG. 8B presses the movable lever 142 toward the housing portion 168a by urging.

The user puts a finger between the housing portion 168a in the outer circumferential surface of the base body 56 and the distal end 142b of the movable lever 142. Thus, when a state in which the movable lever 142 is housed in, for example, the housing portion 168a against the urging force of the torsion spring 146b is 0 degrees, the movable lever 142 can be suitably raised to the extent of about 90 degrees. The user can attach to or detach from the proximal side probe unit 12 with smaller force when the user rotates the distal ends 142b of the raised movable levers 142 around the central axis C2 than when the user grasps the outer circumferential surface 68a of the base body 56 to rotate the outer circumferential surface 68a around the central axis C2 for attachment to or detachment from the proximal side probe unit 12.

Next, a fifth modification of the first embodiment is described with reference to FIG. 9A to FIG. 9C.

In this modification, a jig (attachment/detachment auxiliary tool) 210 used to attach and detach the distal side probe unit 14 to and from the proximal side probe unit 12 is mainly described.

Figure 9A:
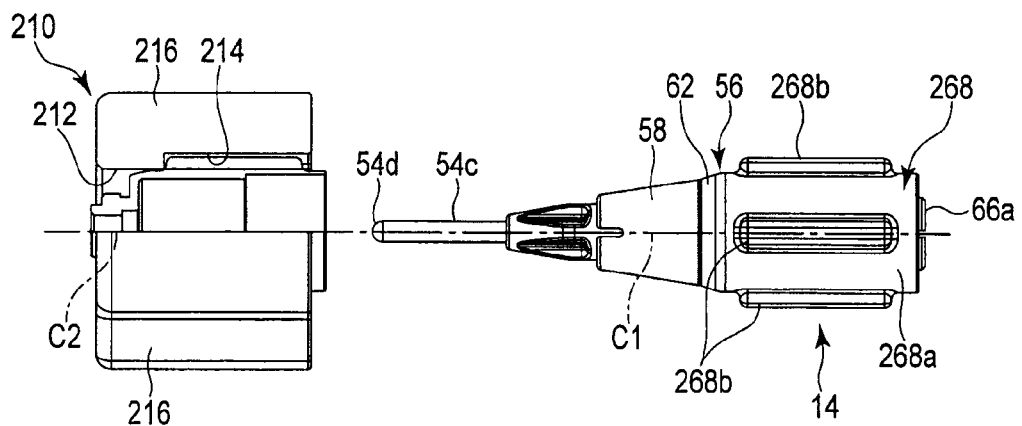
FIG. 9A is a schematic side view showing a state where a jig which can be used in attachment/detachment for the proximal side probe unit is placed to face the distal side probe unit of the treatment instrument according to a fifth modification of the first embodiment.

As shown in FIG. 9A to FIG. 9C, in this modification, the base body 56 has a cylindrical body 268 covering the second connection portion 60 continuously with the base portion 62 on the proximal side relative to its central axis C2. Protrusions (rotating torque applying portions) 268b are formed in an outer circumferential surface 268a of the cylindrical body 268. Although only one protrusion 268b may be formed in the outer circumferential surface 268a of the cylindrical body 268 of the base portion 62, the protrusions 268b are formed, for example, at positions staggered 90 degrees in the circumferential direction relative to the central axis C2 in this modification. That is, in this modification, the base body 56 has four protrusions 268b in the outer circumferential surface 268a of the cylindrical body 268.

The jig (rotating torque applying portion) 210 includes a fit cylinder 212 having recesses 214 which are fitted to the protrusions 268b disposed in the outer circumferential surface 268a of the base body 56 of the distal side probe unit 14, and a pair of wing portions (rotating torque applying portions) 216 which are formed in the outer circumferential surface of the fit cylinder 212 and which are further from the central axis C2 as compared to the tops of the protrusions 268b formed in the outer circumferential surface 268a of the cylindrical body 268.

When the proximal side probe unit 12 and the distal side probe unit 14 are attached to each other, the fit cylinder 212 of the jig 210 is fitted to the outer circumferential surface 63 of the base portion 62 of the base body 56 through the treatment portion 54d and the rotation knob 58. In this state, the user grasps the outside of the exterior case 26 of the proximal side probe unit 12 with the other hand to rotate the exterior case 26 relative to the jig 210 so that the central axes C1 and C2 are in alignment. Since the wing portions 216 are located more distal to the central axis C2 than the outer circumferential surface 63 of the base portion 62, greater torque can be generated with smaller force than when the outer circumferential surface 63 of the base portion 62 is directly grasped. Thus, the user can easily attach the proximal side probe unit 12 and the distal side probe unit 14 to each other with small force against the urging force of the urging body 86 by using the jig 210.

When the proximal side probe unit 12 and the distal side probe unit 14 are detached from each other as well, the user can easily detach the proximal side probe unit 12 and the distal side probe unit 14 from each other with small force against the urging force of the urging body 86 by using the jig 210.

The protrusions 268b formed in the outer circumferential surface 268a of the base body 56 of the distal side probe unit 14 according to this modification also function as non-slips. The tops of the protrusions 268b are located more distal to the central axis C2 than the outer circumferential surface 268a of the base body 56. Thus, it is possible to attach the proximal side probe unit 12 and the distal side probe unit 14 to each other and detach the proximal side probe unit 12 and the distal side probe unit 14 from each other solely by use of the protrusions 268b formed in the outer circumferential surface 268a of the base body 56. The jig 210 may be used when it is difficult to attach or detach the distal side probe unit 14 to or from the proximal side probe unit 12 even if the protrusions 268b formed in the outer circumferential surface 268a of the base body 56 are grasped.

In the example described here, the protrusions 268b are formed in the outer circumferential surface 268a of the cylindrical body 268 of the base body 56, and the recesses 214 are formed in the fit cylinder 212 of the jig 210. It is also preferable that protrusions protruding toward the central axis C2 are formed in the fit cylinder 212 of the jig 210 and fitted into the recesses formed as the non-slips in the outer circumferential surface 268a of the cylindrical body 268 of the base body 56.

Next, a sixth modification of the first embodiment is described with reference to FIG. 10 to FIG. 12B.

Figure 10:
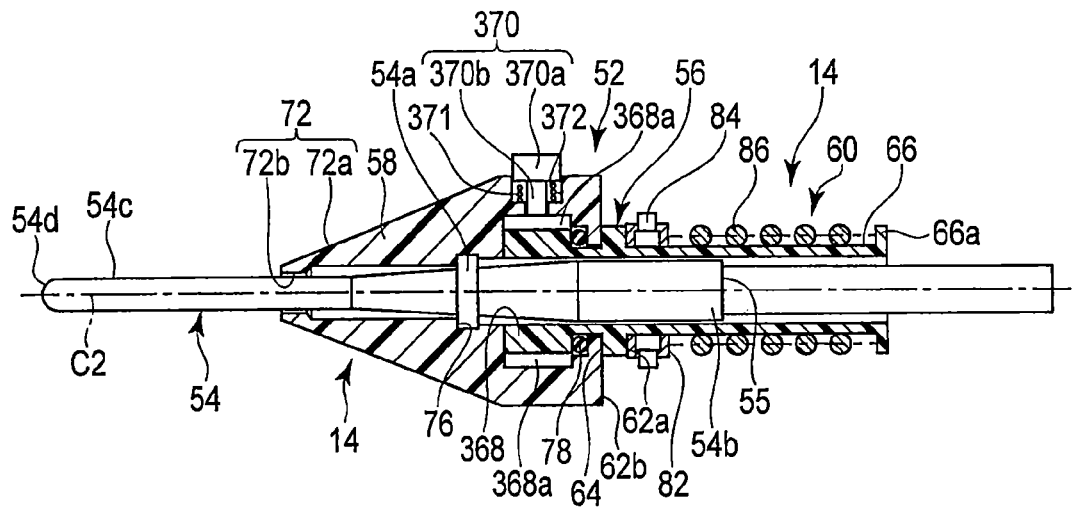
FIG. 10 is a schematic longitudinal sectional view showing the distal side probe unit of the treatment instrument according to a sixth modification of the first embodiment.
Figure 11:
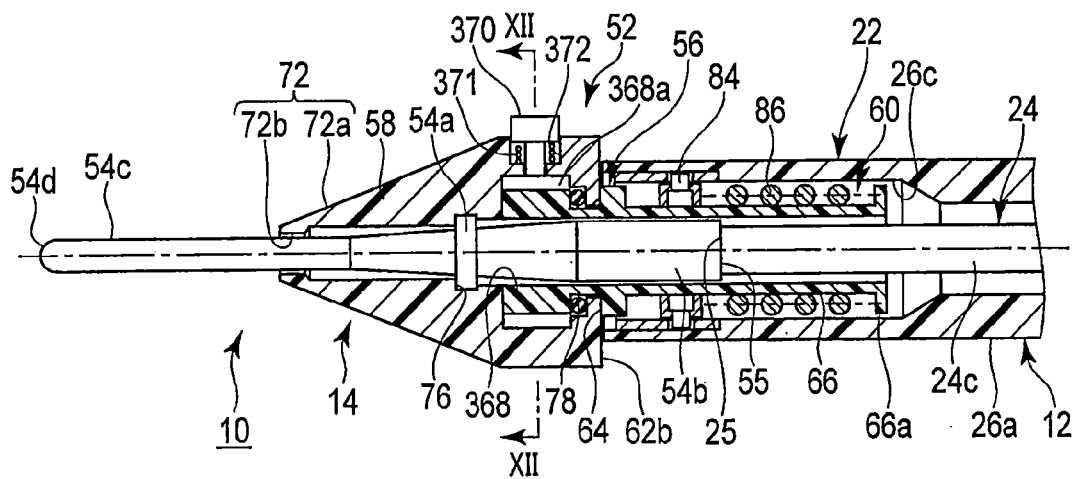
FIG. 11 is a schematic longitudinal sectional view showing a state where the proximal side probe unit and the distal side probe unit of the treatment instrument according to the sixth modification of the first embodiment are attached.
Figure 12A:
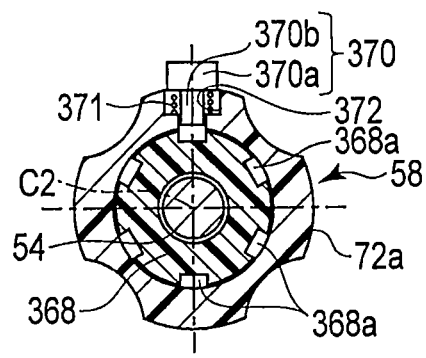
FIG. 12A is a schematic cross sectional view taken along the line XII-XII in FIG. 10 of the treatment instrument according to the sixth modification of the first embodiment, showing a state where a press pin is released.
Figure 12B:
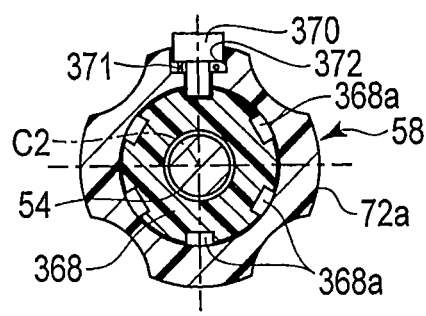
FIG. 12B is a schematic cross sectional view taken along the line XII-XII in FIG. 10 of the treatment instrument according to the sixth modification of the first embodiment, showing a state where the press pin is pressed toward a central axis.

As shown in FIG. 10 and FIG. 11, the base portion 62 (see FIG. 1A) is not formed in the base body 56 of the distal side probe unit 14 in the treatment instrument 10 according to this modification. The base body 56 includes an integral knob coupling portion 64 and tube portion 66. An extending cylinder 368 having fit slots 368a in the outer circumference is formed at the distal end of the knob coupling portion 64.

A through-hole 372 which pierces in the diametrical direction that intersects at right angles with the central axis C2 is formed in the knob main body 72 of the rotation knob 58. A press pin 370 which can be moved by an urging body 371 in a direction that intersects at right angles with the central axis C2 and which is diametrically outwardly urged is supported in the through-hole 372. If the user presses a distal end 370a of the press pin 370 toward the central axis C2, a central side end 370b close to the central axis C2 can be moved toward the central axis C2 against the urging force of the urging body 371. In this instance, the central side end 370b of the press pin 370 can be fitted in one of the fit slots 368a.

The urging body 371 of the press pin 370 has smaller urging force than the urging body 86 of the second connection portion 60, and can easily let the press pin 370 into the through-hole 372 of the rotation knob 58 and fit the press pin 370 into the fit slot 368a if the press pin 370 is pressed with the finger of one hand.

In this modification, the base portion 62 of the base body 56 is not present as discussed previously. Thus, when the unshown hand switch to switch on/off the output to the ultrasonic transducer 31 is disposed in the treatment instrument 10, the hand switch is preferably disposed not in the base body 56 of the distal side probe unit 14 but in the exterior case 26 of the proximal side probe unit 12.

Next, functions of the treatment instrument 10 according to this modification are briefly described.

When the distal side probe unit 14 is attached to the proximal side probe unit 12, the distal end 370*a* of the press pin 370 of the rotation knob 58 of the distal side probe unit 14 is pressed closer to the central axis C2. Accordingly, the central side end 370*b* enters one of the fit slots 368*a* of the extending cylinder 368. This prevents the rotation of the rotation knob 58 relative to the base body 56. In this state, as has been described in the first embodiment, the exterior case 26 of the proximal side probe unit 12 is grasped with, for example, the right hand, the press pin 370 is pressed and the rotation knob 58 is also grasped with the left hand, and then the distal side probe unit 14 is attached to the proximal side probe unit 12.

When a treatment is conducted by the use of ultrasonic vibration, the finger is taken off the press pin 370 to release the press pin 370. In this instance, the central side end 370*b* of the press pin 370 escapes from the fit slot 368*a* by the urging force of the urging body 371.

The press pin 370 is released, and the exterior case 26, the ultrasonic transducer unit 30, and the proximal side vibration transmission body 24 of the proximal side probe unit 12 are kept located as they are, in which state the rotation knob 58 is rotated around the central axis C2. In this instance, the central side end 370*b* of the press pin 370 is not disposed in the fit slot 368*a*, the flange portion 54*a* of the distal side vibration transmission body 54 which is whirl-stopped on the support portion 76 of the rotation knob 58 rotates relative to the proximal side vibration transmission body 24 and the ultrasonic transducer unit 30 which are whirl-stopped on the exterior case 26.

Thus, the distal side vibration transmission body 54 can be rotated around the central axes C1 and C2 in a state where the proximal side vibration transmission body 24, the exterior case 26, and the ultrasonic transducer unit 30 of the proximal side probe unit 12 are kept located as they are. It is therefore possible to direct the treatment portion 54*d* in a suitable direction relative to the proximal side vibration transmission body 24, the exterior case 26, and the ultrasonic transducer unit 30 of the proximal side probe unit 12.

When the proximal side probe unit 12 and the distal side probe unit 14 are detached from each other, the press pin 370 is pressed to fit the central side end 370*b* into one of the fit slots 368*a*. While this state is maintained, the proximal side probe unit 12 and the distal side probe unit 14 are rotated in the directions opposite to the directions to attach the distal side probe unit 14 to the proximal side probe unit 12.

That is, in this modification, the rotation knob (operation portion) 58 and the distal side holding portion (holding portion) 52 have the regulation portions 368*a* and 370 which regulate rotation around the first and second central axes C1 and C2 relative to each other. The regulation portions 368*a* and 370 can selectively regulate and deregulate rotation of the distal side holding portion 52 around the first and second central axes C1 and C2 relative to each other.

According to the treatment instrument 10 in this embodiment, the proximal side probe unit 12 and the distal side probe unit 14 cannot be separated unless the press pin 370 of the distal side probe unit 14 is pressed toward the central axis C2 and the central side end 370*b* of the press pin 370 is fitted in the fit slot 368*a*. It is therefore possible to certainly prevent the proximal side probe unit 12 and the distal side probe unit 14 from being unintentionally separated during the use of the treatment instrument 10.

Next, a seventh modification of the first embodiment is described with reference to FIG. 13A to FIG. 14B.

Figure 14A:
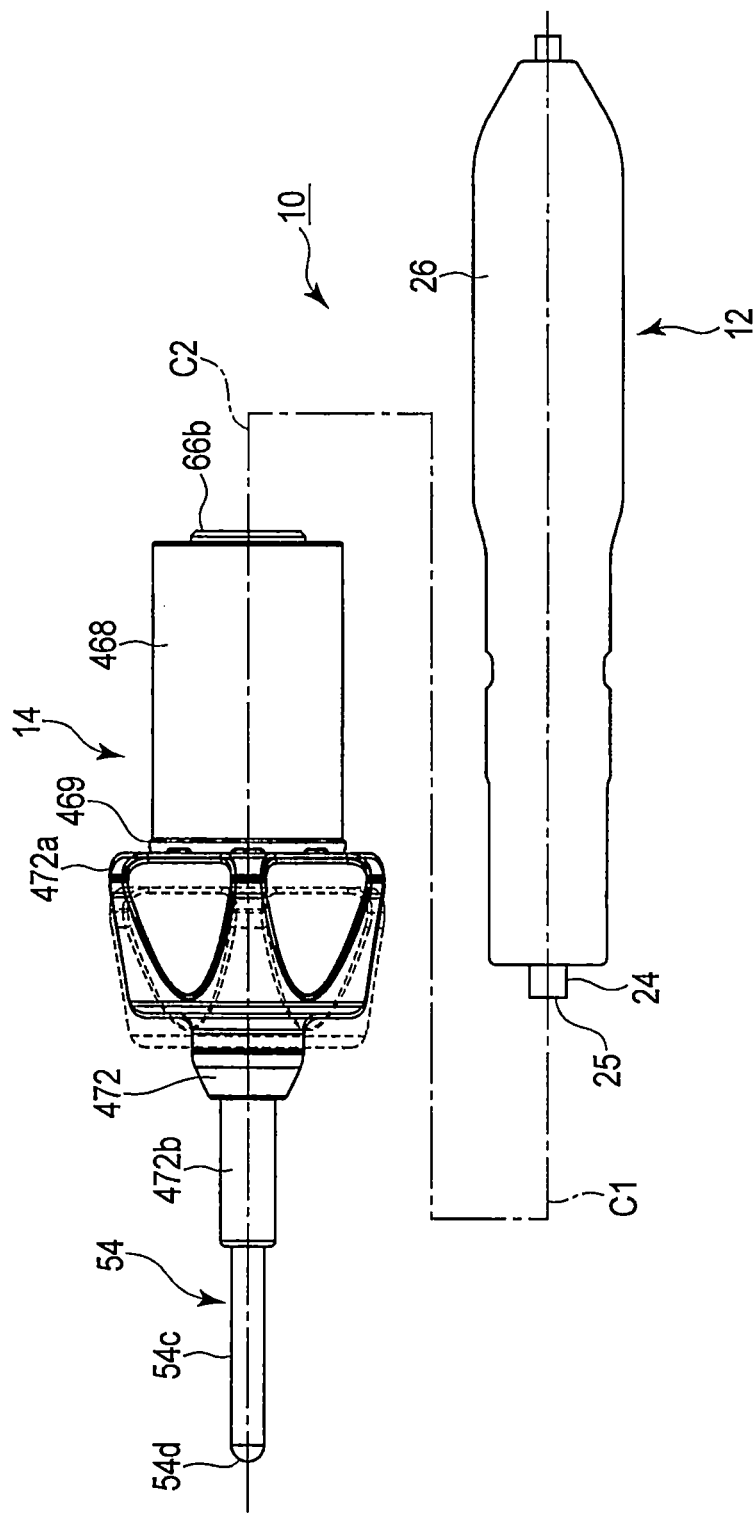
FIG. 14A is a schematic side view showing a state where the proximal side probe unit and the distal side probe unit according to an eighth modification of the first embodiment are separated.

The difference between the proximal side probe unit 12 in this modification and the proximal side probe unit 12 described in the first embodiment is the position of the distal surface 25 of the proximal side vibration transmission body 24 relative to the distal end of the exterior case 26 of the proximal side probe unit 12. As shown in FIG. 14A, in this modification, the distal surface 25 of the proximal side vibration transmission body 24 is closer to the distal side along the central axis C1 than the distal end of the exterior case 26 of the proximal side probe unit 12.

Figure 13A:
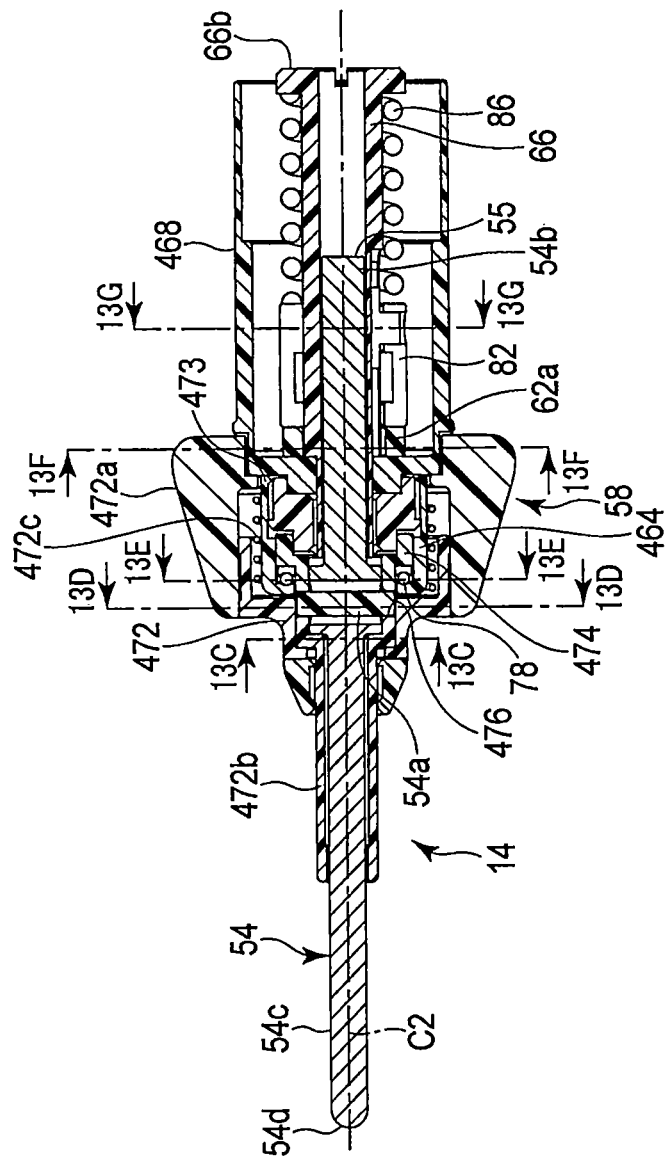
FIG. 13A is a schematic longitudinal sectional view showing the distal side probe unit of the treatment instrument according to a seventh modification of the first embodiment.
Figure 13B:
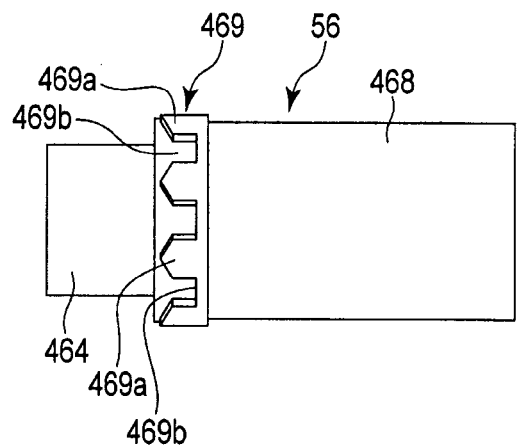
FIG. 13B is a schematic side view showing the cylindrical body of the distal side probe unit of the treatment instrument according to the seventh modification of the first embodiment.
Figure 13C:
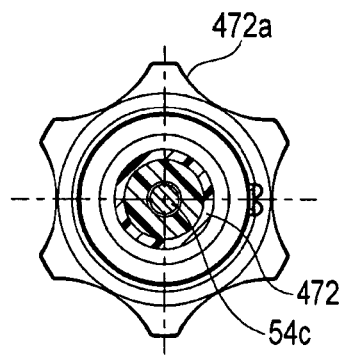
FIG. 13C is a schematic cross sectional view taken along the line 13C-13C in FIG. 13A.

As shown in FIG. 13A and FIG. 13B, the base body 56 according to this modification has a cylindrical body 468 concentric with the central axis C2 outside the tube portion 66. A fit portion 469 is formed annularly in the circumferential direction of the central axis C2 in the outer circumferential surface of the distal end of the cylindrical body 468. The fit portion 469 alternately has protrusions 469*a* and fit slots 469*b*. Each of the protrusions 469*a* is formed to taper off along the central axis C2. Later-described projections 473 of the rotation knob 58 can be put in and out of the fit slots 469*b* parallel to the central axis C2.

A cylindrical knob coupling portion 464 is formed on the distal side of the base body 56.

The rotation knob 58 according to this modification includes a knob main body 472, an operation body 472*a*, and a sheath 472*b*. The knob main body 472 and the sheath 472*b* are integrated (see FIG. 13A and FIG. 13C).

As shown in FIG. 13A, the distal side vibration transmission body 54 is inserted through the knob main body 472. The operation body 472*a* is provided in the outer circumference of the knob main body 472. The operation body 472*a* is urged toward the proximal side along the central axis C2 relative to the knob main body 472 by an urging body 472*c* such as a coil spring. The urging body 472*c* is provided between the outer circumferential surface of the knob coupling portion 464 and the inner circumferential surface of the knob main body 472. One end (distal end) of the urging body 472*c* is supported on the knob main body 472, and the other end (proximal end) is supported on the operation body 472*a*. As shown in FIG. 13A and FIG. 13F, the projections 473 which can be put in and out of the fit slots 469*b* of the fit portion 469 of the cylindrical body 468 are formed at positions where the other end of the urging body 472*c* is supported in the operation body 472*a*. The projections 473 protrude toward the central axis C2 from the inner circumferential surface of the operation body 472*a*. The urging body 472*c* has smaller urging force (press force) than the urging body 86 which urges the slider 82 to the distal side along the central axis C2.

If the operation body 472*a* is moved to the distal side of the direction of the central axis C2 against the urging force of the urging body 472*c* (see broken lines in FIG. 14A and FIG. 14B), the projections 473 come out of the fit slots 469*b* of the cylindrical body 468 so that the operation body 472*a* becomes rotatable relative to the cylindrical body 468 around the central axis C2. In the meantime, if the operation body 472*a* is released, the projections 473 urged by the urging force of the urging body 472*c* are put into the fit slots 469*b* (see solid lines in FIG. 14A and FIG. 14B). In this instance, since the protrusions 469*a* of the fit portion 469 are tapered, the projections 473 are guided to the fit slots 469*b* regardless of the position of the operation body 472*a* relative to the cylindrical body 468. Thus, the protrusions 469*a* of the fit portion 469 are used to guide the projections 473 of the fit slots 469*b*.

Figure 13D:
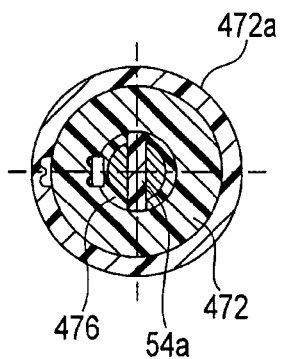
FIG. 13D is a schematic cross sectional view taken along the line 13D-13D in FIG. 13A.

As shown in FIG. 13A, FIG. 13D, and FIG. 13E, a knob main body 472 and the operation body 472a are whirl-stopped. Thus, the knob main body 472 and the operation body 472a rotate around the central axis C2 together even if the operation body 472a is moved to the distal side in the direction of the central axis C2.

As shown in FIG. 13F, the projections 473 in the inner circumferential surface of the operation body 472a are preferably formed at suitable intervals. Here, the number of the fit slots 469b is preferably larger than the number of the projections 473.

The sheath 472b has a base body coupling portion 474 and a support portion 476. The base body coupling portion 474 is coupled to the knob coupling portion 464 of the base body 56. The support portion 476 supports the flange portion 54a of the distal side vibration transmission body 54 in a whirl-stopped state. The sheath 472b protects a suitable part of the second vibration transmitting portion 54c protruding from the knob main body 472 by, for example, a heat-resistant and friction-resistant material such as a PTFE material.

Next, functions of the treatment instrument 10 according to this modification are described.

When the proximal side probe unit 12 and the distal side probe unit 14 are attached to each other, for example, the proximal side probe unit 12 is grasped with the right hand, and the distal side probe unit 14 is grasped with the left hand. In this instance, the left hand grasps the cylindrical body 468 of the distal side probe unit 14, or grasps the cylindrical body 468 together with the operation body 472a in a state where the operation body 472a is at a solid line position in FIG. 14A. As shown in FIG. 14A, the distal end of the proximal side probe unit 12 and the proximal end of the distal side probe unit 14 are relatively rotated around the central axes C1 and C2 and then fitted together. In this instance, the operation body 472a is held at the solid line position.

When the direction of the treatment portion 54d is changed relative to the ultrasonic transducer unit 30 and the proximal side vibration transmission body 24, the operation body 472a is moved to a broken line position against the urging force of the urging body 472c in a state where the proximal side probe unit 12 and the distal side probe unit 14 are attached to each other as shown in FIG. 14B. That is, the projections 473 of the operation body 472a are removed from the fit slots 469b. When the operation body 472a is at the broken line position, the projections 473 of the operation body 472a are out of the fit slots 469b. Thus, the operation body 472a is rotatable around the central axis C2.

In this instance, the operation body 472a rotates integrally with the knob main body 472, the sheath 472b, and the distal side vibration transmission body 54. Thus, if the operation body 472a which has been moved to the broken line position is rotated around the central axis C2, the direction of the treatment portion 54d can be changed relative to the cylindrical body 468 of the base body 56 and the proximal side probe unit 12. If the operation body 472a is released in this state, the projections 473 of the operation body 472a are fitted into the fit slots 469b by the urging force of the urging body 472c. Thus, a suitable treatment can be conducted in a state where the treatment portion 54d faces in a desired direction relative to the cylindrical body 468 of the base body 56 and the proximal side probe unit 12. In this instance, the number of the fit slots 469b present in the circumferential direction of the cylindrical body 468 is larger than the number of the projections 473. Thus, the direction of the treatment portion 54d can be finely adjusted around the central axis C2.

When the distal side probe unit 14 is detached and separated from the proximal side probe unit 12, the distal side probe unit 14 is rotated relative to the proximal side probe unit 12 around the central axes C1 and C2 in a direction opposite to the direction at the time of attachment in a state where the operation body 472a is disposed at a position indicated by the solid line in FIG. 14B.

That is, in this modification, the rotation knob (operation portion) 58 and the distal side holding portion (holding portion) 52 have the regulation portions 469, 472a, 472c, and 473 which regulate rotation around the first and second central axes C1 and C2 relative to each other. The regulation portions 469, 472a, 472c, and 473 can selectively regulate and deregulate rotation of the distal side holding portion 52 around the first and second central axes C1 and C2 relative to each other.

According to the treatment instrument 10 in this embodiment, it is possible to change the rotation position of the operation body 472a of the rotation knob 58 relative to the base body 56, that is, the direction of the treatment portion 54d by a suitable angle. Thus, the user can always keep the position of the treatment portion 54d relative to the exterior case 26 of the proximal side probe unit 12 and the base body 56 of the distal side probe unit 14 at a desired suitable angle. Therefore, the user can decide the direction of the treatment portion 54d to a familiar position relative to the exterior case 26 of the proximal side probe unit 12 and the base body 56 of the distal side probe unit 14. It is thus easy for the user to conduct a treatment using the treatment instrument 10.

Figure 15:
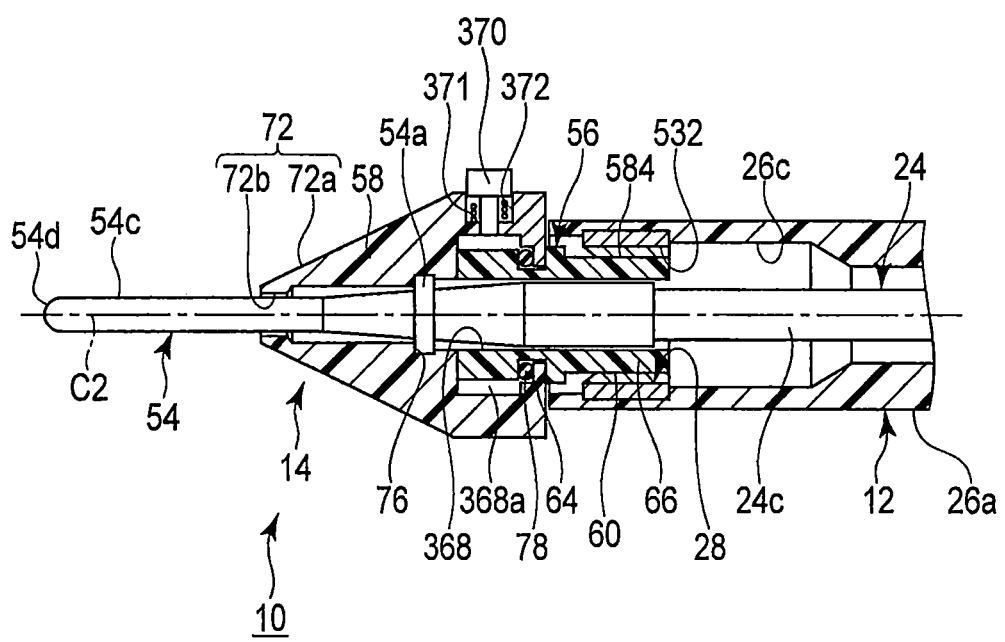
FIG. 15 is a schematic longitudinal sectional view showing a state where the proximal side probe unit and the distal side probe unit of the treatment instrument according to a second embodiment are attached.

Next, the second embodiment is described with reference to FIG. 15. This embodiment is a modification of the first embodiment including its modifications. The same components or components having the same functions as those described in the first embodiment are provided with the same reference signs as much as possible, and are not described in detail. This embodiment is described as a modification of the sixth modification (see FIG. 10 to FIG. 12B) of the first embodiment.

The difference between the treatment instrument 10 according to this embodiment and the treatment instrument 10 described in the first embodiment is the coupling structure of the proximal side probe unit 12 and the distal side probe unit 14. In the example of the treatment instrument 10 according to this embodiment, the proximal side probe unit 12 and the distal side probe unit 14 are fastened by screws to be coupled. The distal side probe unit 14 according to this embodiment does not require the urging body 86, the slider 82, and the cam pin 84 that have been described in the first embodiment. The proximal side probe unit 12 does not require the cam ring 32 having the cam groove 34 either.

The first connection portion 28 in the inner circumferential surface of the exterior case 26 of the proximal side probe unit 12 has an internal thread 532 in the inner circumferential surface of the housing portion 26c. The second connection portion 60 of the distal side probe unit 14 has an external thread 584 in the outer circumferential surface of the tube portion 66.

Here, the press pin 370 of the rotation knob 58 is pressed to dispose the central side end 370b in the fit slot 368a, in which state the internal thread 532 and the external thread 584 are screwed together. That is, the rotation knob 58 and the base body 56 are integrally turned relative to the proximal side probe unit 12. Thus, the internal thread 532 and the external thread 584 are screwed together. The internal thread 532 and the external thread 584 are screwed together so that the distal surface 25 of the proximal side vibration transmission body 24 of the proximal side probe unit 12 is brought into collision with the proximal side collision portion 55 of the distal side vibration transmission body 54 of the distal side probe unit 14.

In this instance, the internal thread 532 and the external thread 584 are kept screwed together, for example, even if an attempt is made to operate the rotation knob 58 while the exterior case 26 is being grasped with the right hand and the press pin 370 is being pressed with the finger of the right hand.

Even when the treatment instrument 10 is formed as above, the distal side probe unit 14 can be attached to and detached from the proximal side probe unit 12 without the need of any exclusive tool, and the treatment portion 54*d* can be rotated to a desired position relative to the proximal side probe unit 12 in a state where the distal side probe unit 14 is suitably attached to the proximal side probe unit 12, as in the treatment instrument 10 described in the first embodiment.

Next, the third embodiment is described with reference to FIG. 16A to FIG. 16F. This embodiment is a modification of the first embodiment and the second embodiment including their modifications. The same components or components having the same functions as those described in the first embodiment and the second embodiment are provided with the same reference signs as much as possible, and are not described in detail.

The difference between the treatment instrument 10 according to this embodiment and the treatment instrument 10 described in the first and second embodiments is the coupling structure of the proximal side probe unit 12 and the distal side probe unit 14.

As shown in FIG. 16A to FIG. 16F, the treatment instrument 10 according to this embodiment has the proximal side probe unit 12, the distal side probe unit 14, a cylindrical adapter 616 which attaches and detaches the proximal side probe unit 12 and the distal side probe unit 14.

The distal side probe unit 14 has the distal side vibration transmission body 54, the base body 56, and a sheath unit 658. In this embodiment, the base body 56 and the sheath unit 658 are fixed to each other by, for example, screwing.

Figure 16B:
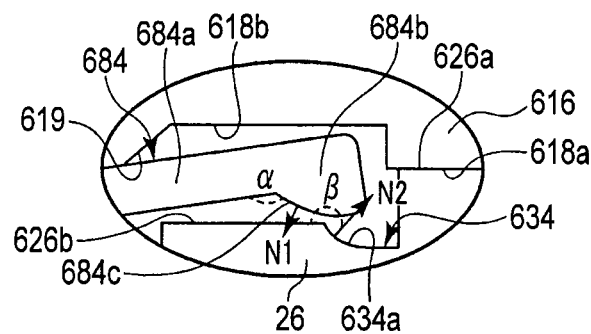
FIG. 16B is an enlarged view of a part elliptically enclosed in FIG. 16A.
Figure 16C:
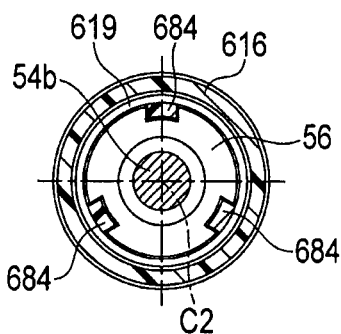
FIG. 16C is a schematic cross sectional view taken along the line 16C-16C in FIG. 16A.
Figure 16D:
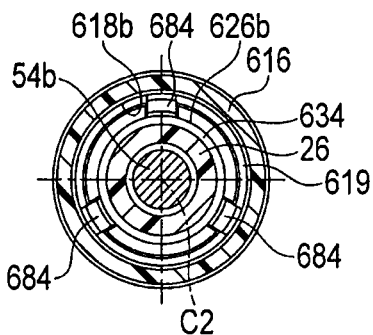
FIG. 16D is a schematic cross sectional view taken along the line 16D-16D in FIG. 16A.

The inner circumferential surface of the base body 56 has the support portion 76 which supports the flange portion 54*a* of the distal side vibration transmission body 54 in a whirl-stopped state. The outer circumferential surface of the base body 56 includes a major outside diameter portion 656*a* and a minor outside diameter portion 656*b* from the proximal side to the distal side. A fit portion 662 to which a later-described fit portion 618*d* of the adapter 616 is fitted, and pawl receiving portions 663 which receive pawls 618*e* are formed in the outer circumferential surface of the base body 56. The fit portion 662 is located at the boundary between the major outside diameter portion 656*a* and the minor outside diameter portion 656*b*. The pawl receiving portions 663 are formed in the minor outside diameter portion 656*b*. The fit portion 662 is annularly formed. On the other hand, as shown in FIG. 16F, more than one pawl receiving portion 663, for example, three pawl receiving portions 663 are formed every 120 degrees relative to the central axis C2.

Chuck portions 684 are formed at the proximal end of the base body 56. As shown in FIG. 16C and FIG. 16D, more than one chuck portion 684, for example, three chuck portions 684 are formed every 120 degrees relative to the central axis C2. Each of the chuck portions 684 has an extension 684*a* extending toward the proximal side of the central axis C2 from the proximal end of the base body 56 to the proximal side, and a pawl 684*b* which is formed at the position of the extension 684*a* distal to the proximal end of the base body 56 and which is housed in a chuck housing portion 634 of the proximal side probe unit 12. The extension 684*a* of the chuck portion 684 diametrically outwardly extends and protrudes relative to the outer circumferential surface of the base body 56. That is, the chuck portion 684 is elastically deformably bent.

The pawl 684*b* protrudes toward the central axis C2 at the distal position of the extension 684*a*. As shown in FIG. 16B, the pawl 684*b* has an inclined plane 684*c* which defines a normal N1 toward the distal side of the central axis C2 from the position where the pawl 684*b* is formed. An angle α between the inclined plane 684*c* and the extension 684*a* is an obtuse angle of 90 to 180 degrees.

The distal end of the exterior case 26 has a major outside diameter portion 626*a* and a minor outside diameter portion 626*b* from the proximal side to the distal side. The recessed chuck housing portion 634 in which the chuck portion 684 is housed is formed between the major outside diameter portion 626*a* and the minor outside diameter portion 626*b*. The chuck housing portion 634 is formed annularly around the central axis C1. The chuck housing portion 634 has an inclined plane 634*a* which is farther from the central axis C1 than the position where the chuck housing portion 634 is formed and which defines a normal N2 toward the proximal side. An angle β between the inclined plane 634*a* and the minor outside diameter portion 626*b* ranges between 180 degrees and 270 degrees.

The adapter 616 has, from the proximal side to distal side of its inner circumferential surface, a slide surface 618*a*, a recess 618*b*, a holding surface 618*c*, the fit portion 618*d*, and the pawls 618*e*.

The slide surface 618*a* inserts the distal side of the distal side probe unit 14, and is disposed in the outer circumferential surface of the major outside diameter portion 626*a* of the exterior case 26 of the base body 56 and the proximal side probe unit 12 in a state where the proximal side probe unit 12 and the distal side probe unit 14 are located at the positions shown in FIG. 16A. The recess 618*b* returns to a state where the chuck portion 684 diametrically outwardly extends after the slide surface 618*a* has passed over the outside of the chuck portion 684. The recess 618*b* has a distal side inclined plane 619 which is used when the adapter 616 is attached to the proximal side probe unit 12 and the distal side probe unit 14.

Figure 16E:
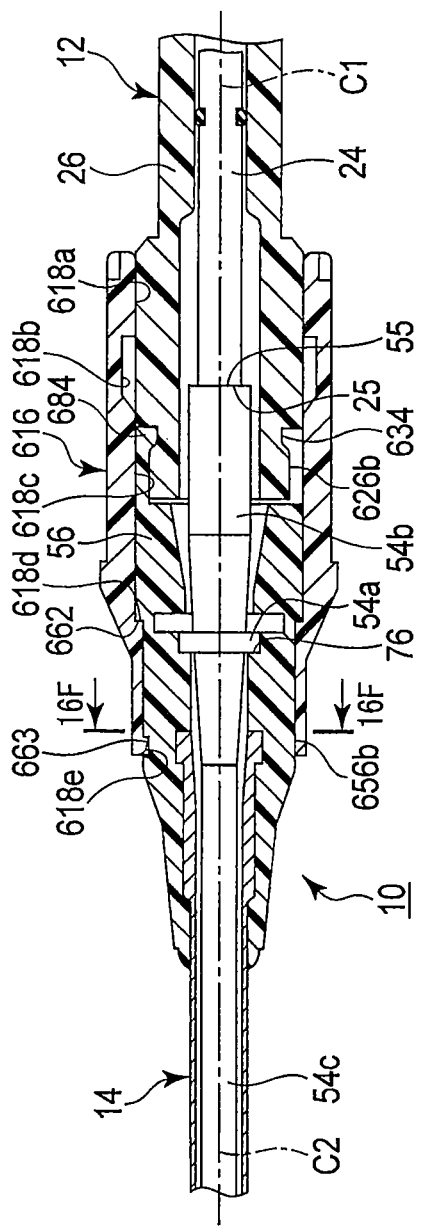
FIG. 16E is a schematic longitudinal sectional view showing a state where the adaptor which couples the proximal side probe unit to the distal side probe unit is disposed at the coupling position while the proximal side probe unit and the distal side probe unit of a treatment instrument according to the third embodiment are disposed on the same central axis.
Figure 16F:
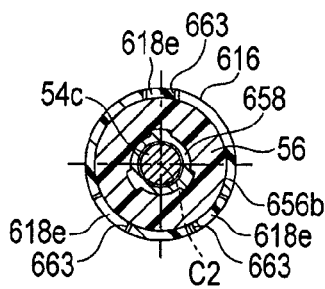
FIG. 16F is a schematic cross sectional view taken along the line 16F-16F in FIG. 16E.

As shown in FIG. 16E, the holding surface 618*c* holds the chuck portion 684 housed in the chuck housing portion 634. The fit portion 618*d* is fitted to the fit portion 662 of the base body 56, and is used to position the adapter 616 relative to the base body 56.

The adapter 616 includes the pawls 618*e* at the distal end therein which are fitted to the pawl receiving portions 663 of the base body 56. Each of the pawls 618*e* has an inclined plane 618*f* by which a normal N is defined toward the distal side in the central axis C2.

The outer circumferential surface of the adapter 616 is preferably formed so that slipping is prevented during the movement relative to the outer circumferential surface of the proximal side probe unit 12 in the directions of the central axes C1 and C2 and around the central axes C1 and C2.

The unshown hand switch is preferably disposed at a position closer to the proximal side of the major outside diameter portion 626*a* of the exterior case 26.

Next, functions of the treatment instrument 10 according to this embodiment are described.

The attachment of the proximal side probe unit 12, the distal side probe unit 14, and the adapter 616 in a suitable state is described.

The central axis C1 of the proximal side vibration transmission body 24 disposed inside the exterior case 26 of the proximal side probe unit 12 is aligned with the central axis C2 of the distal side vibration transmission body 54 disposed inside the base body 56 and the sheath unit 658 of the distal side probe unit 14. In this state, the collision portion 25 of the proximal side vibration transmission body 24 of the proximal side probe unit 12 is brought into collision with the collision portion 55 of the distal side vibration transmission body 54 of the distal side probe unit 14. The adapter 616 is then moved to the outer circumferential surface of the exterior case 26 of the proximal side probe unit 12 through the outer circumferential surface of the base body 56 of the distal side probe unit 14 up to the position shown in FIG. 16A. In this instance, as shown in FIG. 16A, the chuck portion 684 is outside the chuck housing portion 634.

If the adapter 616 is then moved relative to the proximal side probe unit 12 and the distal side probe unit 14 along the directions of the central axes C1 and C2, the recess 618b of the adapter 616 moves to the outside of the major outside diameter portion 626a of the exterior case 26. In this instance, the chuck portion 684 is pressed toward the chuck housing portion 634 of the proximal side probe unit 12 by the distal side inclined plane 619. The chuck portion 684 is then housed in the chuck housing portion 634 of the proximal side probe unit 12 by the holding surface 618c. Further, the fit portion 618d is fitted to the fit portion 662 of the base body 56. The pawls 618e at the distal end of the adapter 616 are engaged with the pawl receiving portions 663 in the outer circumferential surface of the base body 56.

In this instance, by the action of the inclined planes 684c and 634a defining the normals N1 and N2 as shown in FIG. 16B, the collision portion 25 of the proximal side vibration transmission body 24 of the proximal side probe unit 12 is kept in collision with the collision portion 55 of the distal side vibration transmission body 54 of the distal side probe unit 14 while force is applied thereto. The holding surface 618c regulates the diametrically outward protrusion of the chuck portion 684.

Thus, vibration is transmitted to the distal side vibration transmission body 54 from the ultrasonic transducer unit 30 through the proximal side vibration transmission body 24 by suitable operation of the hand switch.

Next, the change of the direction of the treatment portion 54d relative to the proximal side vibration transmission body 24, the exterior case 26, and the ultrasonic transducer unit 30 is described.

The adapter 616 and the base body 56 are whirl-stopped because the pawls 618e and the pawl receiving portions 663 are fitted to each other. On the other hand, the chuck housing portion 634 is annularly formed so that the chuck portion 684 is rotatable relative to the exterior case 26 of the proximal side probe unit 12. Therefore, for example, the user grasps the exterior case 26 with the right hand, and grasps the adapter 616 and/or the distal end of the base body 56 with the left hand to rotate the adapter and the base body 56 relative to the exterior case 26 around the central axes C1 and C2. Thus, the direction of the treatment portion 54d is changed relative to the ultrasonic transducer unit 30 and the proximal side vibration transmission body 24.

The detachment of the adapter 616 from the proximal side probe unit 12 and the distal side probe unit 14 is described.

For example, force is applied in opposite directions along the central axes C1 and C2 in a state where the proximal side probe unit 12 or the distal side probe unit 14 and the adapter 616 are held. The pawls 618e of the adapter 616 climb over the pawl receiving portions 663 of the distal side probe unit 14 to move to the distal side of the central axis C2. The inclined plane 618f of each of the pawls 618e defines the normal N toward the distal side of the central axis C2, so that once disengaged from the pawl receiving portions 663, the adapter 616 can be easily moved to the position shown in FIG. 16A relative to the distal side probe unit 14.

In a state where the chuck portion 684 is disposed in the recess 618b, for example, the user grasps the exterior case 26 of the proximal side probe unit 12 with the right hand, and grasps the outer circumferential surface of the adapter 616 with the left hand to move the proximal side probe unit 12 and the adapter 616 in a direction away from each other along the central axes C1 and C2. The adapter 616 presses the chuck portion 684 toward the distal side along the central axis C2 at the boundary between the slide surface 618a and the recess 618b. Consequently, the distal side probe unit 14 is separated from the proximal side probe unit 12 together with the adapter 616.

Even when the treatment instrument 10 is formed as above, the distal side probe unit 14 can be attached to and detached from the proximal side probe unit 12 without the need of any exclusive tool, and the treatment portion 54d can be rotated to a desired position relative to the proximal side probe unit 12 in a state where the distal side probe unit 14 is suitably attached to the proximal side probe unit 12, as in the treatment instrument 10 described in the first and second embodiments.

Next, the fourth embodiment is described with reference to FIG. 17A to FIG. 18. This embodiment is a modification of the first to third embodiments including their modifications. The same components or components having the same functions as those described in the first to third embodiments are provided with the same reference signs as much as possible, and are not described in detail.

The difference between the treatment instrument 10 according to this embodiment and the treatment instrument 10 described in the first to third embodiments is the coupling structure of the proximal side probe unit 12 and the distal side probe unit 14.

Figure 17A:
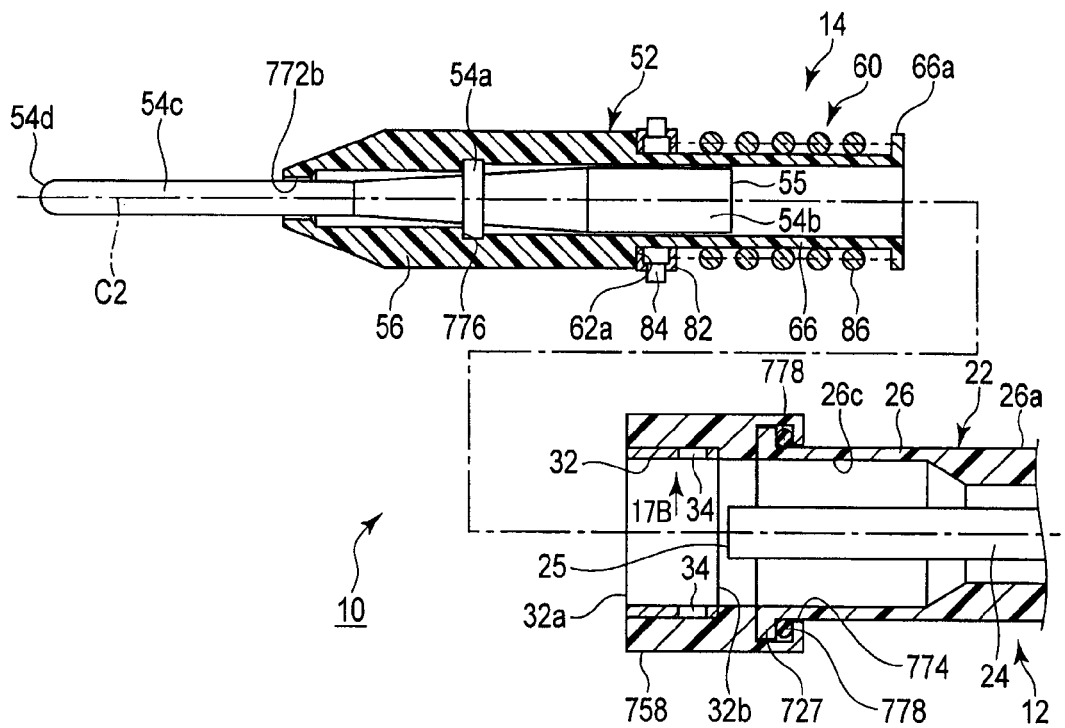
FIG. 17A is a schematic longitudinal sectional view showing a state where the proximal side probe unit and the distal side probe unit according to a fourth embodiment are separated.

As shown in FIG. 17A and FIG. 18, in this embodiment, the rotation knob 58 (see FIG. 1A) is not disposed in the distal side probe unit 14, but a rotation knob 758 is disposed in the proximal side probe unit 12.

A knob coupling portion 727 is formed at the distal end of the exterior case 26 of the proximal side probe unit 12 in the treatment instrument 10 according to this embodiment, and the rotation knob 758 is disposed in the knob coupling portion 727. A case coupling portion 774 which is coupled to the knob coupling portion 727 of the exterior case 26 is formed in the rotation knob 758. Balls 778 are provided between the knob coupling portion 727 and the case coupling portion 774, and reduce friction between the knob coupling portion 727 and the case coupling portion 774.

Figure 17B:
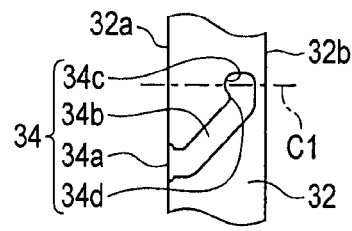
FIG. 17B is a schematic diagram showing the cam ring having the cam groove seen from the direction of an arrow 17B line in FIG. 17A.

The cam ring 32 in which the cam groove 34 is formed is disposed in the inner circumferential surface of the rotation knob 758. As shown in FIG. 17B, the cam groove 34 is formed in the same manner as the cam groove described in the first embodiment.

The rotation knob 58 is eliminated in the distal side probe unit 14 as described above. Thus, the knob coupling portion 64 at the distal end of the base body 56 is removed. On the other hand, a support portion 776 which supports the flange portion 54a of the distal side vibration transmission body 54 in a whirl-stopped state is formed in the inner circumferential surface of the base body 56 of the distal side probe unit 14. The inner circumferential surface at the distal end of the base body 56 is formed as a support portion 772b which supports the second vibration transmitting portion 54c of the distal side vibration transmission body 54 to be able to rotate or turn around the central axis C2.

Next, functions of the treatment instrument 10 according to this embodiment are briefly described.

The attachment of the proximal side probe unit 12 and the distal side probe unit 14 is first described.

As shown in FIG. 17A, the distal end of the proximal side vibration transmission body 24 of the proximal side probe unit 12 is brought into collision with the proximal end of the distal side vibration transmission body 54 of the distal side probe unit 14. In this instance, the cam pin 84 is disposed in the opening 34a of the cam groove 34. In this state, for example, the user grasps the base body 56 with the left hand, and grasps the rotation knob 758 with the right hand to relatively rotate the base body 56 and the rotation knob 758 around the central axes C1 and C2 against the urging force of the urging body 86. Accordingly, the cam pin 84 is engaged with the engagement portion 34c.

When the direction of the treatment portion 54d is changed, the user grasps the exterior case 26 with the right hand to turn the rotation knob 758 around the central axis C1 with the left hand. In response to the rotation of the rotation knob 758, the base body 56 and the distal side vibration transmission body 54 of the distal side probe unit 14 rotate together. Thus, the direction of the treatment portion 54d is changed relative to the exterior case 26, the ultrasonic transducer unit 30, and the proximal side vibration transmission body 24.

When the distal side probe unit 14 is detached from the proximal side probe unit 12, the user grasps the rotation knob 758 with the right hand, and grasps the base body 56 of the distal side probe unit 14 with the left hand. The proximal side probe unit 12 and the distal side probe unit 14 are rotated in the directions opposite to the directions of the attachment, and are thereby separated from each other.

Even when the treatment instrument 10 is formed as above, the distal side probe unit 14 can be attached to and detached from the proximal side probe unit 12 without the need of any exclusive tool, and the treatment portion 54d can be rotated to a desired position relative to the proximal side probe unit 12 in a state where the distal side probe unit 14 is suitably attached to the proximal side probe unit 12, as in the treatment instrument 10 described in the first to third embodiments.

The levers (rotating torque applying portions) 142 shown in FIG. 7 to FIG. 8B or the jig (rotating torque applying portion) 210 shown in FIG. 9A to FIG. 9C can be naturally disposed in the treatment instrument 10 shown in FIG. 17A and FIG. 18.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
    a proximal side probe including a proximal end and a distal end, the proximal side probe extending along a first central axis defined by the proximal end and the distal end, the proximal side probe transmitting ultrasonic vibration from an ultrasonic transducer from the proximal end to the distal end along the first central axis;
    a distal side probe including a proximal end and a distal end, the distal side probe extending along a second central axis defined by the proximal end and the distal end, the distal side probe having a treatment portion, and the distal side probe being configured to transmit ultrasonic vibration from the proximal end to the treatment portion at the distal end of the distal side probe along the second central axis;
    a holding portion having a casing, the holding portion being configured to hold the distal side probe and the proximal side probe in a state where:
        the proximal end of the distal side probe is brought into contact with the distal end of the proximal side probe,
        vibration from the ultrasonic transducer is transmittable from the proximal end of the proximal side probe to the distal end of the distal side probe,
        the first central axis is aligned with the second central axis, and
        the casing is directly fixed to the proximal side probe; and
    an operation portion provided in the holding portion and being configured to turn or rotate the distal side probe independently relative to the proximal side probe around the first central axis and the second central axis by an operation of the operation portion to rotate the distal side probe around the first central axis and the second central axis, to direct the treatment portion at the distal end of the distal side probe in a desired direction.

2. The treatment instrument according to claim 1, wherein the holding portion includes an urging body which presses the distal end of the proximal side probe and the proximal end of the distal side probe with a constant force.

3. The treatment instrument according to claim 1, wherein the proximal side probe is disposed in the casing; and
    the holding portion includes a distal side holding portion which is attachable to and detachable from the case and which holds the distal side probe therein.

4. The treatment instrument according to claim 3, wherein the operation portion is coupled to the distal side holding portion rotatably around the second central axis.

5. The treatment instrument according to claim 3, wherein the operation portion is coupled to the casing rotatably around the first central axis.

6. The treatment instrument according to claim 3, further comprising:
    an attachment/detachment mechanism which:
        attaches the casing and the distal side holding portion to each other while bringing the distal end of the proximal side probe and the proximal end of the distal side probe into contact with each other, and
        detaches the casing and the distal side holding portion from each other while bringing the distal end of the proximal side probe and the proximal end of the distal side probe out of contact with each other.

7. The treatment instrument according to claim 6, wherein the attachment/detachment mechanism is configured to attach and detach the casing and the distal side holding portion to and from each other by relatively turning or rotating the casing and the distal side holding portion around the first central axis and the second central axis.

8. The treatment instrument according to claim 7, wherein the attachment/detachment mechanism includes a rotating torque applying portion disposed in the outer circumference of at least one of the casing and the distal side holding portion.

9. The treatment instrument according to claim 8, wherein the rotating torque applying portion includes a movable portion which is configured to increase and decrease in outside diameter.

10. The treatment instrument according to claim 8, wherein the rotating torque applying portion is attachable to and detachable from the distal side holding portion.

11. The treatment instrument according to claim 6, wherein the attachment/detachment mechanism includes a mechanism which is configured to attach and detach the casing and the distal side holding portion by movement in an axial direction.

12. The treatment instrument according to claim 1, wherein the operation portion and the holding portion includes a regulation portion which regulates rotation around the first central axis and the second central axis relative to each other.

13. The treatment instrument according to claim 12, wherein the regulation portion selectively regulates and deregulates rotation of the holding portion around the first central axes and the second central axis relative to each other.

14. The treatment instrument according to claim 1, wherein in the condition where the distal end of the proximal side probe is in contact with the proximal end of the distal side probe, a contact part of the proximal side probe and the distal side probe is located at or in the vicinity of an antinode position of vibration when the vibration is transmitted to the distal end of the distal side probe from the ultrasonic transducer through the proximal side probe.

15. The treatment instrument according to claim 1, wherein the distal side probe has a length of an integer multiple of a half wavelength of ultrasonic vibration of the ultrasonic transducer.

16. The treatment instrument according to claim 1, wherein the ultrasonic transducer is fixed to the proximal end of the proximal side probe.

17. The treatment instrument according to claim 1, wherein the proximal end of the proximal side probe is coupled to the distal end of an ultrasonic probe.

18. A treatment instrument comprising:
an end effector which extends along a first central axis;
a vibration transmission probe which extends along a second central axis, being configured to transmit ultrasonic vibration from a proximal end of the vibration transmission probe to a distal end of the vibration transmission probe along the second central axis;
a cylindrical body configured to receive the end effector;
a case which retains the vibration transmission probe in the case, being configured to connect to the cylindrical body so as to prevent a relative rotation between the cylindrical body and the case when the vibration transmission probe coaxially contacts the end effector; and
a knob which is rotatably attached to the cylindrical body and holds the end effector in the knob, wherein a rotation of the knob causes the end effector to rotate independently relative to the vibration transmission probe in a condition that the cylindrical body is connected to the case.

19. The treatment instrument according to claim 18, further comprising:
a cam mechanism configured to lock the relative rotation in a rotation direction about the first central axis and the second central axis.

20. The treatment instrument according to claim 19, wherein the cam mechanism comprises a cam pin and a cam groove.

21. The treatment instrument according to claim 20, wherein the cam groove extends around the first central axis or the second central axis.

\* \* \* \* \*